US008663937B2

(12) United States Patent
St-Arnaud

(10) Patent No.: US 8,663,937 B2
(45) Date of Patent: **\*Mar. 4, 2014**

(54) CLONED TRANSMEMBRANE RECEPTOR FOR 24-HYDROXYLATED VITAMIN D COMPOUNDS AND USES THEREOF

(71) Applicant: Shriners Hospital For Children, Tampa, FL (US)

(72) Inventor: Rene St-Arnaud, St-Laurent (CA)

(73) Assignee: Shriners Hospital For Children, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/906,014

(22) Filed: May 30, 2013

(65) Prior Publication Data

US 2013/0252252 A1    Sep. 26, 2013

Related U.S. Application Data

(60) Division of application No. 13/306,599, filed on Nov. 29, 2011, which is a continuation of application No. PCT/US2010/036842, filed on Jun. 1, 2010.

(60) Provisional application No. 61/182,951, filed on Jun. 1, 2009.

(51) Int. Cl.
*G01N 33/53* (2006.01)
*C12Q 1/68* (2006.01)
*G01N 33/567* (2006.01)

(52) U.S. Cl.
USPC ............ 435/7.2; 435/6.13; 435/7.1; 435/7.21

(58) Field of Classification Search
None
See application file for complete search history.

(56) References Cited

U.S. PATENT DOCUMENTS

| | | | |
|---|---|---|---|
| 4,439,196 A | 3/1984 | Higuchi | |
| 4,447,224 A | 5/1984 | DeCant, Jr. et al. | |
| 4,447,233 A | 5/1984 | Mayfield | |
| 4,475,196 A | 10/1984 | La Zor | |
| 4,486,194 A | 12/1984 | Ferrara | |
| 4,487,603 A | 12/1984 | Harris | |
| 4,522,811 A | 6/1985 | Eppstein et al. | |
| 4,596,556 A | 6/1986 | Morrow et al. | |
| 4,790,824 A | 12/1988 | Morrow et al. | |
| 4,941,880 A | 7/1990 | Burns | |
| 5,064,413 A | 11/1991 | McKinnon, Jr. et al. | |
| 5,312,335 A | 5/1994 | McKinnon, Jr. et al. | |
| 5,383,851 A | 1/1995 | McKinnon, Jr. et al. | |
| 5,399,163 A | 3/1995 | Peterson et al. | |
| 2012/0180142 A1 | 7/2012 | St-Arnaud | |
| 2013/0252250 A1 | 9/2013 | St-Arnaud | |
| 2013/0254910 A1 | 9/2013 | St-Arnaud | |

OTHER PUBLICATIONS

Akhouayri, et al., "Sequence-Specific DNA Binding by the αNAC Coactivator is Required for Potentiation of c-Jun-Dependent Transcription of the Osteocalcin Gene", *Molecular and Cellular Biology*, 25(9):3452-3460 (2005).
Akhouayri, et al., "Differential Mechanisms of Transcriptional Regulation of the Mouse Osteocalcin Gene by Jun Family Members", *Calcified Tissue International*, 80:123-131 (2007).
Altschul, et al., "Basic Local Alignment Search Tool", *J. Mol. Biol.*, 215:403-410 (1990).
Altschul, et al., "Gapped BLAST and PSI-BLAST: a new generation of protein database search programs", *Nucleic Acids Research*, 25(17):3389-3402 (1997).
Andreassen, et al., "Intermittent Parathyroid Hormone (1-34) Treatment Increases Callus Formation and Mechanical Strength of Healing Rat Fractures", *Journal of Bone and Mineral Research*, 14(6);960-968 (1999).
Andreassen, et al., "Increases in Callus Folination and Mechanical Strength of Healing Fractures in Old Rats Treated with Parathyroid Hormone", *Acta Orthop Scand.*, 72(3):304-307 (2001).
Andrews, et al., "A Rapid Micropreparation Technique for Extraction of DNA-Binding Proteins from Limiting Numbers of Mammalian Cells", *Nucleic Acids Research*, 19(9):2499 (1991).
Aronson, Experimental and Clinical experience with Distraction Osteogenesis, *Cleft Palate-Craniofacial Journal*, 31(6):473-482 (1994).
Aspenberg, "Drugs and Fracture Repair", *Acta Orthopaedica*, 76(6):741-748 (2005).
Barnes, et al., "Growth Factor Regulation of Fracture Repair", *Journal of Bone and Mineral Research*, 14(11):1805-1815 (1999).
Bonnarens, et al., "Production of a Standard Closed Fracture in Laboratory Animal Bone", *Journal of Orthopaedic Research*, 2:97-101 (1984).
Bouillon, et al., "Structure-Function Relationships in the Vitamin D Endocrine System", *Endocrine Reviews*, 16(2):200-257 (1995).
Bouillon, et al., "Vitamin D and Human Health: Lessons from Vitamin D Receptor Null Mice", *Endocrine Reviews*, 29(6):726-776 (2008).
Boyan, et al., "Cartilage and vitamin D: Genomic and Nongenomic Regulation by $1,25(OH)_2D_3$ and $24,25(OH)_2D_3$", 2nd Edition, D. Feldman, J.W. Pike and F.H. Glorieux, Elsevier Academic Press, San Diego, Chapter 33:575-597 (2005).
Boyan, et al., "Evidence for Distinct Membrane Receptors for $1\alpha,25$-$(OH)_2D_3$ and $24R,25$-$(OH)_2D_3$ in Osteoblasts", *Steroids*, 67:235-246 (2002).
Bradley, et al., "Formation of Germ-Line Chimaeras from Embryo-Derived Teratocarcinoma Cell Lines", *Nature*, 309:255-256 (1984).
Brighton, et al., "Early Histological and Ultrastructural Changes in Medullary Fracture Callus", *The Journal of Bone and Joint Surgery*, 73:832-847 (1991).
Candeliere, et al., "A Composite Element Binding the Vitamin D Receptor, Retinoid X Receptor α, and a Member of the CTF/NF-1 Family of Transcription Factors Mediates the Vitamin D Responsiveness of the c-*fos* Promoter", *Molecular and Cellular Biology*, 19(9):2499 (1991).

(Continued)

*Primary Examiner* — Doug Schultz
(74) *Attorney, Agent, or Firm* — Baker Botts LLP

(57) ABSTRACT

The instant invention relates to the use of 24-hydroxylated vitamin D compounds as therapeutics in mammalian bone fracture repair. In addition, the instant invention relates to novel 24-hydroxylated vitamin D compound receptors which can be employed in the development of compounds capable of facilitating fracture repair in animals. The instant invention also relates to nucleic acids encoding such receptors as well as vectors, host cells, transgenic animals comprising such nucleic acids and screening assays employing such receptors.

6 Claims, 5 Drawing Sheets

(56) References Cited

OTHER PUBLICATIONS

Ciambrone, et al., "Cellular Dielectric Spectroscopy: A Powerful New Approach to Label-Free Cellular Analysis", *The Society for Biomolecular Screening*, 9(6):467-480 (2004).
Colnot, et al., "Altered Fracture Repair in the Absence of MMP9", *Development*, 130:4123-4133 (2003).
Copeland, et al., "Recombineering: A Powerful New Tool for Mouse Functional Genomics", *Nature Reviews/Genetics*, 2:769-779 (2001).
Corsini, et al., "New Insights into the Pharmacodynamic and Pharmacokinetic Properties of Statins", *Pharmacology & Therapeutics*, 84:413-428 (1999).
Courey, et al., "Analysis of Sp1 In Vivo Reveals Multiple Transcriptional Domains, Including a Novel Glutamine-Rich Activation Motif", *Cell*, 55:887-898 (1988).
Court, et al., "Genetic engineering Using Homologous Recombination", *Annu. Rev. Genet.*, 36:361-388 (2002).
Dacquin, et al., "Mouse α1(I)-Collagen Promoter Is the Best Known Promoter to Drive Efficient Cre Recombinase Expression in Osteoblast", *Developmental Dynamics*, 224:245-251 (2002).
Dardenne, et al., "Rescue of the Pseudo-Vitamin D Deficiency Rickets Phenotype of CYP27B1-Deficient Mice by Treatment with 1,25-Dihydroxyvitamin $D_3$: Biochemical, Histomorphometric, and Biomechanical Analyses", *Journal of Bone and Mineral research*, 18(4):637-643 (2003).
Dardenne, et al., "Targeted Inactivation of the 25-Hydroxyvitamin $D_3$-$1_\alpha$-Hydorxylase Gene (CYP27B1) Creates an Animal Model of Pseudovitamin D-Deficiency Rickets", *Endocrinology*, 142(7):3135-3414 (2001).
Dardenne, et al., "Correction of the Abnormal Mineral Ion Homeostasis with a High-Calcium, High-Phosphorus, High-Lactose Diet Rescues The PDDR Phenotype of Mice Deficient for the 25-Hydroxyvitamin D-1α-Hydroxylase (CYP27B1)", *Bone*, 32:332-340 (2003).
DeLuca, "Overview of General Physiologic Features and Function of Vitamin $D^{1-4}$", *Am. J. Clin. Nutr.*, 80(Suppl):1689S-1696S (2004).
Evans, et al., "Establishment in Culture of Pluripotential Cells from Mouse Embroys", *Nature*, 292:154-156 (1981).
Ferguson, et al., "Does Adult Fracture Repair Recapitulate Embryonic Skeletal Formation?", *Mechanisms of Development*, 87:57-66 (1999).
Gossler, et al., "Transgenesis by Means of Blastocyst-Derived Embryonic Stem Cell Lines", *PNAS*, 83:9065-9069 (1986).
Govender, et al., "Recombinant Human Bone Morphogenetic Protein-2 for Treatment of Open Tibial Fractures: A Prospective, Controlled, Randomized Study of Four Hundred and Fifty Patients", *The Journal of Bone and Joint Surgery*, 84:2123-2134 (2002).
Hadjiargyrou, et al., "Transcriptional Profiling of Bone Regeneration", *The Journal of Biological Chemistry*, 277(33):30177-30182 (2002).
Hague, et al., "Characterizing the BMP Pathway in a wild Type Mouse Model of Distraction Osteogenesis", *Bone*, 42:1144-1153 (2008).
Hatano, et al., "Identification of Estrogen-Regulated Genes During Fracture Healing, Using DNA Microarray", *Journal of Bone and Mineral Metabolism*, 22:224-235 (2004).
Hess, et al., "Proteins S-Nitrosylation: Purview and Parameters", *Nature Reviews Molecular Cell Biology*, 6:150-166 (2005).
Holick, et al., "Prevalence of Vitamin D Inadequacy Among Postmenopausal North American Women Receiving Osteoporosis Therapy", *The Journal of Clinical Endocrinology & Metabolism*, 90(6):3215-3224 (2005).
Holick, et al., "Chemical Synthesis of [1β-$^3$H] 1α, 25-Dihydroxyvitamin $D_3$ and [1α-$^3$H] 1β, 25-Dihydroxyvitamin $D_3$: Biological Activity of 1β, 25-Dihydroxyvitamin $D_3$", *Biochemical and Biophysical Research Communications*, 97(3):1031-1037 (1980).
Horst, et al., "Vitamin D Metabolism", *2nd Edition, D. Feldman, J.W Pike and F.H. Glorieux, Elsevier Academic Press, San Diego*, Chapter 2:15-36 (2005).

Jaenisch, "Germ Line Integration and Mendelian Transmission of the Exogenous Moloney Leukemia Virus", *PNAS*, 73(4):1260-1264 (1976).
Jaenisch, "Transgenic Animals", *Science*, 240:1468-1474 (1988).
Jähner, et al., "Insertion of the Bacterial *gpt* Gene into the Germ Line of Mice by Retroviral Infection", *PNAS*, 82:6927-6931 (1985).
Jähner, et al., "De Novo Methylation and Expression of Retroviral Genomes During Mouse Embryogenesis", *Nature*, 298:623-628 (1982).
Johnson, et al., "An Improved Permeabilization Protocol for the Introductio of Peptides into Cardiac Myocytes", *Circulation Research*, 79:1086-1099 (1996).
Jones, et al., "Current Understanding of the Molecular Actions of Vitamin D", *Physiological Reviews*, 78(4):1193-1231 (1998).
Kato, et al., "Studies on 24R, 25-Dihydroxyvitamin $D_3$: Evidence for a Nonuclear Membrane Receptor in the Chick Tibial Fracture-Healing Callus", *Bone*, 23(2):141-146 (1998).
Kroll, et al., "A Multifunctional Prokaryotic Protein Expression System: Overproduction, Affinity Purification, and Selective Detection", *DNA and Cell Biology*, 12(5):441-453 (1993).
Laird, et al., "Simplified Mammalian DNA Isolation Procedure", *Nucleic Acids Research*, 19(15):4293 (1991).
Li, et al., "A Novel, Non-Prostanoid EP2 Receptor-Selective Prostaglandin $E_2$ Agonist Stimulates Local Bone Formation and Enhances Fracture Healing", *Journal of Bone and Mineral Research*, 18(11):2033-2042 (2003).
Makin, et al., "Target Cell Metabolism of 1, 25-Dihydroxyvitamin $D_3$ to Calcitroic Acid", *Biochem J.*, 262:173-180 (1989).
Mansour, et al., "disruption of the Proto-Oncogene *int*-2 in Mouse Embryo-Derived Stem Cells: A General Strategy for Targeting Mutations to Non-Selectable Genes", *Nature*, 336:348-352 (1988).
Masuda, et al., "Altered Pharmacokinetics of 1α, 25-Dihydroxyvitamin $D_3$ and 25-Hydroxyvitamin $D_3$ in the Blood and Tissues of the 25-Hydroxyvitamin D-24-Hydroxylase (Cyp24a1) Null Mouse", *Endocrinology*, 146(2):825-834 (2005).
Minkowitz, et al., "Effects of Propranolol on Bone Metabolism in the Rat", *Journal of Orthopaedic Research*, 9:869-875 (1991).
Mitchell, et al., "Polyarginine Enters Cells More Efficiently Than Other Polycationic Homopolymers", *J. Peptide Res.*, 56:318-325 (2000).
Moreau, et al., "Bone-Specific Expression of the Alpha Chain of the Nascent Polypeptide-Associated Complex, a Coactivator Potentiating c-Jun-Mediated Transcription", *Molecular and Cellular Biology*, 18(3):1312-1321 (1998).
Mulder, et al., "Drug Insight: Existing and Emerging Therapies for Osteoporosis", *Nature Clinical Practice, Endocrinology & Metabolism*, 2(12):670-680 (2006).
Mundy, et al., "Stimulation of Bone Formation in Vitro and in Rodents by Statins", *Science*, 286:1946-1949 (1999).
Munns, et al., "Delayed Osteotomy but Not Fracture Healing in Pediatric Osteogenesis Imperfecta Patients Receiving Pamidronate", *Journal of Bone and Mineral Research*, 19(10:1779-1786 (2004).
Myers, et al., "Optimal Alignments in Linear Space", *Comput Appl Biosci.*, 4(1):11-17 (1988).
Nagy, et al., "Derivation of Completely Cell Culture-Derived Mice from Early-Passage Embryonic Stem cells", *PNAS*, 90:8424-8428 (1993).
Naik, et al., "Reduced COX-2 Expression in Aged Mice is Associated with Impaired Fracture Healing", *Journal of Bone and Mineral Research*, 24(3):251-264 (2009).
Nakagawa, et al., "Calcium-Dependent Neutral Proteinase (Calpain) in Fracture Healing in Rats", *Journal of Orthopaedic Research*, 12:58-69 (1994).
Nakazawa, et al., "Gene Expression of Periostin in the Early Stage of Fracture Healing Detected by cDNA Microarray Analysis", *Journal of Orthopaedic Research*, 22:520-525 (2004).
Needleman, et al., "A General Method Applicable to the Search for Similarities in the Amino Acid Sequence of Two Proteins", *J. Mol. Biol.*, 48:443-453 (1970).
Omdahl, et al., "Overview of Regulatory Cytochrome P450 Enzymes of the Vitamin D Pathway", *Steroids*, 66:381-389 (2001).

(56) References Cited

OTHER PUBLICATIONS

Paley, "Problems, Obstacles, and Complications of Limb Lengthening by the Ilizarov Technique", *Clinical Orthopaedics and Related Research*, 250:81-104 (1990).

Paralkar, et al., "An EP2 Receptor-Selective Prostaglandin $E_2$ Agonist Induces Bone Healing", *PNAS*, 100(11):6736-6740 (2003).

Patiño, et al., "Characterization of Membrane Receptor Activity for 17α,20β,21-Trihydroxy-4-Pregnen-3-One in Ovaries of Spotted Seatrout (*Cynoscion nebulosus*)", *General and Comparative Endocrinology*, 78:204-217 (1990).

Porath, "Immobilized Metal Ion Affinity Chromatography", *Protein Expression and Purification*, 3:263-281 (1992).

Rauch, et al., "Heart, Brain, and Body Wall Defects in Mice Lacking Calreticulin", *Experimental Cell Research*, 256:105-111 (2000).

Reinhardt, et al., "Ketoconazole Inhibits self-Induces Metabolism of 1,25-Dihydroxyvitamin $D_3$ and Amplifies 1,25-Dihydroxyvitamin $D_3$ Receptor Up-Regulation in Rat Osteosarcoma Cells", *Archives of Biochemistry and Biophysics*, 272(2):459-465 (1989).

Robertson, et al., "Germ-Line Transmission of Genes Introduced into Cultured Pluripotential Cells by Retroviral Vector", *Nature*, 323:445-448 (1986).

Rothbard, et al., "Conjugation of Arginine Oligomers to Cyclosporin A Facilitates Topical Delivery and Inhibition of Inflammation", *Nature Medicine*, 6(11):1253-1257 (2000).

Rucker, et al., "Vitamin D Insufficiency in a Population of Healthy western Canadians", *CMAJ*, 166(12):1517-1524 (2002).

Rundle, et al., "Microarray Analysis of Gene Expression during the Inflammation and Endochondral Bone Formation Stages of Rat Femur Fracture Repair", *Bone*, 38:521-529 (2006).

Sandberg, et al., "In situ Localization of Collagen Production by Chondrocytes and Osteoblasts in Fracture Callus", *The Journal of Bone & Joint Surgery*, 71:69-77 (1989).

Schlienger, et al., "Use of β-Blockers and Risk of Fractures", *JAMA*, 292(11):1326-1332 (2004).

Seeherman, et al., "Delivery of Bone Morphogenetic Proteins for Orthopedic Tissue Regeneration", *Cytokine & Growth Factor Reviews*, 16:329-345 (2005).

Seo, et al., "Three-Fold Induction of Renal 25-Hydroxyvitamin $D_3$-24-Hydroxylase Activity and Increased Serum 24,25-Dihydroxyvitamin $D_3$ Levels Are Correlated with the Healing Process After Chick Tibial Fracture", *Journal of Bone and Mineral Research*, 12(4):598-606 (1997).

Seo, et al., "Evidence for a 24R,25(OH)$_2$-Vitamin $D_3$ Receptor/Binding Protein in a Membrane Fraction Isolated from a Chick Tibial Fracture-Healing Callus", *Biochemical and Biophysical Research Communications*, 225 (Article No. 1154):203-208 (1996).

Seo, et al., "24R,25-Dihydroxyvitamin D3: An essential Vitamin D3 Metabolite for Both Normal Bone Integrity and Healing of Tibial Fracture in Chick", *Endocrinology*, 138(9):3864-3872 (1997).

Simon, et al., "Cyclo-Oxygenase 2 Function is Essential for Bone Fracture Healing", *Journal of Bone and Mineral Research*, 17(6):963-976 (2002).

Skoglund, et al., "Simvastatin Improves Fracture Healing in Mice", *Journal of Bone and Mineral Research*, 17(11):2004-2008 (2002).

Southern, "Detection of Specific Sequences Among DNA Fragments Separated by Gel Electrophoresis", *J. Mol. Biol.*, 98:503-517 (1975).

St.-Arnaud, et al., "*Wnt*-1-Inducing Factor-1: a Novel G/C Box-Binding Transcription Factor Regulating the Expression of *Wnt*-1 During Neuroectodermal Differentiation", *Molecular and Cellular Biology*, 13(3):1590-1598 (1993).

St.-Arnaud, et al., "Deficient Mineralization of Intramembranous Bone in Vitamin D-24-Hydroxylas-Ablated Mice is Due to Elevated 1,25-Dihydroxyvitamin D and Not to the Absence of 24,25-Dihydroxyvitamin D", *Endocrinology*, 141(7):2658-2666 (2000).

Stewart, et al., "Expression of Retroviral Vectors in Transgenic Mice Obtained by Embryo Infection", *The EMBO Journal*, 6(2):383-388 (1987).

Sutton, et al., "Vitamin D: More Than a "Bone-a-Fide" Hormone", *Molecular Endocrinology*, 17(5):777-791 (2003).

Takeda, et al., "Leptin Regulates Bone FOir iation via the Sympathetic Nervous System", *Cell*, 111:305-317 (2002).

Tanaka, et al., "Prostaglandin $E_2$ Receptor (EP4) Selective Agonist (ONO-4819.CD) Accelerates Bone Repair of Femoral cortex After Drill-Hole Injury Associated with Local Upregulation of Bone Turnover in Mature Rats", *Bone*, 34:940-948 (2004).

Tay, et al., "Histochemical and Molecular Analyses of Distraction Osteogenesis in a Mouse Model", *Journal of Orthopaedic Research*, 16:636-642 (1998).

Terpstra, et al., "Reduced Chondrocyte Proliferation and Chondrodysplasia in Mice Lacking the Integrin-Linked Kinase in Chondrocytes", *The Journal of Cell Biology*, 162(1):139-148 (2003).

Theodore, et al., "Intraneural Delivery of Protein Kinase C Pseudosubstrate Leads to Growth Cone Collapse", *The Journal of Neuroscience*, 15(11):7158-7167 (1995).

Thomas, et al., "Hypovitaminosis D in Medical Inpatients", *Journal of Medicine*, 338(12):777-783 (1998).

Toh, et al., "Statins and Fracture Risk. A Systematic Review", *Pharmacoepidemiology and Drug Safety*, 16:627-640 (2007).

Toomik, et al., "A Potential Pitfall in Protein Kinase Assay: Phosphocellulose Paper as an Unreliable Adsorbent of Produced Phosphopeptides", *Analytical Biochemistry*, 204:311-314 (1992).

Van der Putten, et al., "Efficient Insertion of Genes into the Mouse Germ Line Via Retroviral vectors", *PNAS*, 82:6148-6152 (1985).

Warming, et al., "Simple and Highly Efficient BAC Recombineering Using galK Selection", *Nucleic Acids Research*, 33(4):e36 (2005).

Yu, et al., "FIAT represses ATF4-Mediated Transcription to Regulate Bone Mass in Transgenic Mice", *The Journal of Cell Biology*, 169(4):591-601 (2005).

Zhang, et al., "Cyclooxygenase-2 Regulates Mesenchymal Cell Differentiation into the Osteoblast Lineage and is Critically Involved in Bone Repair", *J. Clin. Invest.*, 109:1405-1415 (2002).

FIG.1A  FIG.1B
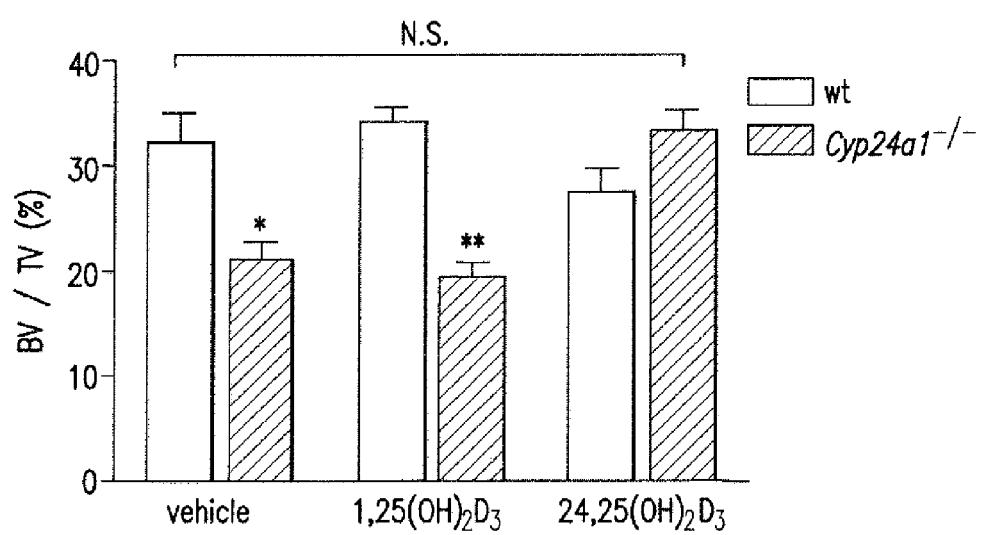
FIG.2

MALLFLLGCVFFPLCFVVLRWGLQNRTSLRMERQEAVLVASKLV
SSVQAIMASTAGYIVSTSCKHIIDDQHWLSSAYTQFAVPYFIYD
IYAMFLCHWHKHQVKGHGGEDGTPRALGSTWAVVRGYLHKEFLM
VLHHAAMVLVCFPLSVVWRQGKGDFFLGCMLMAEVSTPFVCLGK
ILIQYKQQHTLLHKVNGALMLLSFLCCRVLLFPYLYWAYGRHAG
LPLLSVPMAIPAHVNLGAALLLAPQLYWFFLICRGACRLFRPRG
SPPPSPCQTQD (SEQ ID NO: 1)

FIG.3A

```
   1 gctgctgtgg ctcagagctg catgggagac aacgctgctg caggtccggt ttcttggtgt
  61 ctggtcggtg ccatcatttc cctcccctc tcccaccctc ccaagctgg tggcttcccc
 121 tcccctccc cctcctcaca gaggggcag ggggctgggc accaactcta taatgccatg
 181 tgcggtgtct gcacagggca gcggggctct agcggcagca gcaggaggag gtggtagcct
 241 gtggtggcgg gagagcggtg ttgactggtg accgcttgcc cagctgcgcc tccgctccgc
 301 tccgctccgt cctttcctcc ctcccttttt tcagggctgg caccaccgtc cccaccccg
 361 cctccttggg ccctcccagc ctccacgt aagccccccc cccacctgcc gcggttctcc
 421 ctccctccc ccactgcatc ttcctcctcc tgtccctct ccctcttggt cctctcatca
 481 agtcctccct tggtagtctc tccccatcct ctcaccagcg ctctgtcgtc ccccccccc
 541 ccccgccacc tagctagccc tttctttctg tgtccccaat ctcattgaag tccctttctc
 601 ccttgccctg aactggtcct cttgtcccat cctgtccccg ccctggcccc tttgtgcctc
 661 ccctccctc tttctctctc cctttctggc ttggcaatcc cttcttcacc tccaactccc
 721 tccctcaatt tggccttcct gtcccttctg gaccctctgg tctccctgcc cgggttcaag
 781 tcaccatgct taccccaatg gtggctgggg gggtggtgtt ccccggactc ttcctcctat
 841 ccaagaacac gctccagagg ctgccccagc tgcgctggga ggaggccgac gcagtcattg
 901 tctccgccag gttggtgtcc tctgtccaag ccatcatggc ctccacagct ggctacatag
 961 tctccacttc ctgcaagcac atcatagatg accagcactg ctgtcctcg gcctatacac
1021 agtttgcagt tccctacttc atctatgaca tctatgccat gttcctctgc cactggcaca
1081 agcaccaggt taaagggcac ggaggggaag acgggacgcc cagagccctg ggcagcacct
1141 gggctgtggt acgcggctac ctgcacaagg agttcctcat ggtgctccac cacgcggcca
1201 tggtactggt gtgcttccca ctctcagtgg tgtggcgaca aggcaaggga gatttctttc
1261 taggctgcat gttgatggcc gaggtcagca ctcctttcgt ctgcctgggc aagatcctca
1321 ttcagtacaa gcagcagcac acgttgctgc acaaggtgaa cggagccctg atgctactca
1381 gcttcctgtg ctgccgggtg ctgctcttcc cctacctgta ctgggcctac gggcgccacg
1441 ctggcctgcc cctgctctca gtgcccatgg ccatcccggc ccacgtcaac ctgggcgccg
1501 cactgctcct cgcaccccag ctctactggt tcttcctcat ttgccgcggg gcctgccgcc
1561 tcttccgacc ccgaggctcc ccaccaccct ctccttgtca gacccaggac tgaggctagg
1621 ccctggaaac cctcccccc ctccagcccc tgtggagaca gtgcattggg gtaatcagtg
1681 tgtgagttgg gggggggggg acgagagcca gaagtcccct tccttgacag ccccaagaca
1741 gatggactta gaataaggag aagctatatt ccctcgggag ctgaggtcag attggcaggc
1801 aggaagagag gggaccgggg taacgaaccc cttcttgcct ctgtgttaac aaaatgaaag
1861 gggaagggag gagatggggc tcacttggac caaggagtca agggacataa gggtggcccc
1921 gctgccaagg acatcctagc cctgctgctg caaatccttc tctgctcccc atcacccggg
1981 agagagaaga catcctaact cccccacct gggccctgac agggcagtta ccccacagc
2041 cccttcctgt ggagaccagt ccgaggaacc attttattta ttcacccata tcaaactaat
2101 ttgttgggt gaggggagga aggcagttgc tccctacaa cctttccagc gctgagcagc
2161 cctgggaca ggcgccaggc cagtcccttc tgtcagggc acatttagcc ctcggccccg
2221 gcttgtccct ggtgctacag gccaatcgcg gcttcctcca gtctggggc cacagacccc
2281 gggaggtgct tttacagacc gctaataaag acgatcttcc tgaacgccag caaaaaaaaa
2341 aaaaaaaa
```

(SEQ ID NO: 2)

FIG. 3B

SEQUENCE LISTING

```
<160> NUMBER OF SEQ ID NOS: 2

<210> SEQ ID NO 1
<211> LENGTH: 275
<212> TYPE: PRT
<213> ORGANISM: Mus musculus

<400> SEQUENCE: 1

Met Ala Leu Leu Phe Leu Leu Gly Cys Val Phe Phe Pro Leu Cys Phe
1               5                   10                  15

Val Val Leu Arg Trp Gly Leu Gln Asn Arg Thr Ser Leu Arg Met Glu
            20                  25                  30

Arg Gln Glu Ala Val Leu Val Ala Ser Lys Leu Val Ser Ser Val Gln
        35                  40                  45

Ala Ile Met Ala Ser Thr Ala Gly Tyr Ile Val Ser Thr Ser Cys Lys
    50                  55                  60

His Ile Ile Asp Asp Gln His Trp Leu Ser Ser Ala Tyr Thr Gln Phe
65                  70                  75                  80

Ala Val Pro Tyr Phe Ile Tyr Asp Ile Tyr Ala Met Phe Leu Cys His
                85                  90                  95

Trp His Lys His Gln Val Lys Gly His Gly Gly Glu Asp Gly Thr Pro
            100                 105                 110

Arg Ala Leu Gly Ser Thr Trp Ala Val Val Arg Gly Tyr Leu His Lys
        115                 120                 125

Glu Phe Leu Met Val Leu His His Ala Ala Met Val Leu Val Cys Phe
    130                 135                 140

Pro Leu Ser Val Val Trp Arg Gln Gly Lys Gly Asp Phe Phe Leu Gly
145                 150                 155                 160

Cys Met Leu Met Ala Glu Val Ser Thr Pro Phe Val Cys Leu Gly Lys
                165                 170                 175

Ile Leu Ile Gln Tyr Lys Gln Gln His Thr Leu Leu His Lys Val Asn
```

```
                     180                 185                 190
Gly Ala Leu Met Leu Leu Ser Phe Leu Cys Cys Arg Val Leu Leu Phe
            195                 200                 205
Pro Tyr Leu Tyr Trp Ala Tyr Gly Arg His Ala Gly Leu Pro Leu Leu
        210                 215                 220
Ser Val Pro Met Ala Ile Pro Ala His Val Asn Leu Gly Ala Ala Leu
225                 230                 235                 240
Leu Leu Ala Pro Gln Leu Tyr Trp Phe Phe Leu Ile Cys Arg Gly Ala
                245                 250                 255
Cys Arg Leu Phe Arg Pro Arg Gly Ser Pro Pro Ser Pro Cys Gln
            260                 265                 270
Thr Gln Asp
        275

<210> SEQ ID NO 2
<211> LENGTH: 2347
<212> TYPE: DNA
<213> ORGANISM: Mus musculus

<400> SEQUENCE: 2
gctgctgtgg ctcagagctg catgggagac aacgctgctg caggtccggt ttcttggtgt      60
ctggtcggtg ccatcatttc cctcccctc tcccaccctc cccaagctgg tggcttcccc     120 tcccctccc cctcctcaca gagggggcag ggggctgggc accaactcta taatgccatg     180
tgcggtgtct gcacagggca gcggggctct agcggcagca gcaggaggag gtggtagcct     240
gtggtggcgg gagagcggtg ttgactggtg accgcttgcc cagctgcgcc tccgctccgc     300
tccgctccgt cctttcctcc ctcccttttt tcagggctgg caccaccgtc cccacccccg     360
cctccttggg ccctcccagc ctctccacgt aagcccccc cccacctgcc gcggttctcc     420 ctccctccc ccactgcatc ttcctcctcc tgtcccctct ccctcttggt cctctcatca     480 agtcctcct tggtagtctc tccccatcct ctcaccagcg ctctgtcgtc ccccccccc     540 ccccgccacc tagctagccc tttctttctg tgtcccaat ctcattgaag tccctttctc     600
ccttgccctg aactggtcct cttgtcccat cctgtccccg cctggccc tttgtgcctc     660 cccctccctc tttctctctc cctttctggc ttggcaatcc cttcttcacc tccaactccc     720
tccctcaatt tggccttcct gtcccttctg gaccctctgg tctccctgcc cgggttcaag     780
tcaccatgct taccccaatg gtggctgggg gggtggtgtt ccccggactc ttcctcctat     840
ccaagaacac gctccagagg ctgccccagc tgcgctggga ggaggccgac gcagtcattg     900
tctccgccag gttggtgtcc tctgtccaag ccatcatggc ctccacagct ggctacatag     960
tctccacttc ctgcaagcac atcatagatg accagcactg gctgtcctcg gcctatacac    1020
agtttgcagt tccctacttc atctatgaca tctatgccat gttcctctgc cactggcaca    1080
agcaccaggt taaagggcac ggaggggaag acgggacgcc cagagccctg gcagcacct    1140 gggctgtggt acgcggctac ctgcacaagg agttcctcat ggtgctccac cacgcggcca    1200
tggtactggt gtgcttccca ctctcagtgg tgtggcgaca aggcaaggga gatttctttc    1260
taggctgcat gttgatggcc gaggtcagca ctcctttcgt ctgcctgggc aagatcctca    1320
ttcagtacaa gcagcagcac acgttgctgc acaaggtgaa cggagccctg atgctactca    1380
gcttcctgtg ctgccgggtg ctgctcttcc cctacctgta ctgggcctac gggcgccacg    1440
ctggcctgcc cctgctctca gtgcccatgg ccatcccggc ccacgtcaac ctgggcgccg    1500
cactgctcct cgcaccccag ctctactggt tcttcctcat ttgccgcggg gcctgccgcc    1560
```

-continued

```
tcttccgacc ccgaggctcc ccaccaccct ctccttgtca gacccaggac tgaggctagg    1620
ccctggaaac cctccccccc ctccagcccc tgtggagaca gtgcattggg gtaatcagtg    1680
tgtgagttgg ggggggggg acgagagcca gaagtccctt tccttgacag ccccaagaca     1740
gatggactta gaataaggag aagctatatt ccctcgggag ctgaggtcag attggcaggc    1800
aggaagagag gggaccgggg taacgaaccc cttcttgcct ctgtgttaac aaaatgaaag    1860
gggaagggag gagatggggc tcacttggac caaggagtca agggacataa gggtggcccc    1920
gctgccaagg acatcctagc cctgctgctg caaatccttc tctgctcccc atcacccggg    1980
agagagaaga catcctaact cccccacct gggccctgac agggcagtta cccccacagc     2040
cccttcctgt ggagaccagt ccgaggaacc attttattta ttcacccata tcaaactaat    2100
ttgttggggt gaggggagga aggcagttgc tcccctacaa cctttccagc gctgagcagc    2160
cctggggaca ggcgccaggc cagtcccttc tgtcaggggc acatttagcc ctcggccccg    2220
gcttgtccct ggtgctacag gccaatcgcg gcttcctcca gtctgggggc cacagacccc    2280
gggaggtgct tttacagacc gctaataaag acgatcttcc tgaacgccag caaaaaaaaa    2340
aaaaaaa                                                             2347
```

CLONED TRANSMEMBRANE RECEPTOR FOR 24-HYDROXYLATED VITAMIN D COMPOUNDS AND USES THEREOF

CROSS REFERENCE TO RELATED APPLICATIONS

The present application is a Divisional of U.S. application Ser. No. 13/306,599, filed Nov. 29, 2011, which is a continuation of International Patent Application No. PCT/US2010/036842, filed Jun. 1, 2010, published in English on Dec. 9, 2010 as International Patent Publication No. WO10/141,430, which claims priority to U.S. Provisional Application No. 61/182,951, filed Jun. 1, 2009, all of which are incorporated by reference herein in their entireties.

BACKGROUND OF THE INVENTION

Two forms of vitamin D exist in nature: vitamin $D_2$ (ergocalciferol), which is formed in plants by the UV irradiation of the plant product ergosterol, and vitamin $D_3$ (cholecalciferol), which is formed in animal tissues from near-UV (290-310 nm) irradiation of 7-dehydrocholesterol found in keratinocytes (123). In animals, vitamin $D_3$ functions as a key regulator of mineral ion homeostasis, but first the vitamin must undergo two modifications in order to be activated. In the liver, vitamin $D_3$ is initially hydroxylated at position 25, and in the kidney, it is subsequently hydroxylated at position 1 to produce 1,25-$(OH)_2D_3$, the hormonal form of vitamin D (1). Upon reaching its target tissues, 1,25-$(OH)_2D_3$ binds to its specific nuclear receptor, the vitamin D receptor (VDR), to regulate the transcription of vitamin D target genes responsible for carrying out physiological actions including: mineral homeostasis, skeletal homeostasis, and cellular differentiation (2).

The Cyp24a1 gene encodes the CYP24A1 cytochrome P450 enzyme that catalyzes the addition of a hydroxyl group on carbon 24 of the vitamin D secosteroid backbone. When the substrate is 1,25-$(OH)_2D_3$, hydroxylation by CYP24A1 leads to the production of 1,24,25-trihydroxyvitamin $D_3$. 1,24,25-trihydroxyvitamin $D_3$ is the initial reactant in the 24-oxidation pathway that leads to metabolite inactivation (3). Indeed, blocking CYP24A1 cytochrome P450 activity in cell culture systems inhibits catabolism of, and results in increased accumulation of 1,25-$(OH)_2D_3$ (4). The function of the CYP24A1 protein as an effector of 1,25-$(OH)_2D_3$ breakdown has also been confirmed in vivo. For example, mice deficient for the Cyp24a1 gene cannot effectively clear 1,25-$(OH)_2D_3$ from their circulation (5).

The 25-$(OH)D_3$ metabolite can also serve as the substrate for the CYP24A1 enzyme. Use of 25-$(OH)D_3$ as the substrate leads to the production of 24,25-$(OH)_2D_3$. Prior to the filing of this application, the potential bioactivity of 24,25-$(OH)_2D_3$ remained controversial. For example, the literature demonstrates that Cyp24a1 is expressed in growth plate chondrocytes and that cells from the growth plate respond to 24,25-$(OH)_2D_3$ in a cell maturation-dependent manner (6). However, the growth plates from Cyp24a1$^{-/-}$ mice do not show major defects (5). These observations suggested that the absence of CYP24A1 activity does not affect growth plate development and that 24,25-$(OH)_2D_3$ is not required for chondrocyte maturation in vivo.

Another aspect of bone biology in which investigators have sought to identify a role for 24,25-$(OH)_2D_3$ is fracture repair. Traumatic injury is a major public health issue. In the United States, close to 10 million trauma-induced fractures are reported annually (National Center for Health Statistics). United States statistics for the year 2002 reported 54 million office visits, 21 million emergency room visits, 4.5 million outpatient visits and 2 million hospitalizations dealing with traumatic injuries. Of the 2 million hospitalizations, 13 million related to bone fractures (United States Bone and Joint Decade web site, www.usbjd.org). Fractures continue to be the leading cause of injury hospitalization in the United States, accounting for more than one-half of all injury hospitalizations in 2004-2005 (National Center for Health Statistics).

With these traumatic fracture statistics in mind, consideration must also be given to the increase in the incidence of osteoporotic fractures that occurs in individuals after age 65. The aging of the U.S. population will increase the relative impact of musculoskeletal conditions: over the next thirty years, the percent of the population age 65 and over will increase from 12.8% to 20.0%. Individuals 65 years and older, especially women, are more likely to sustain a bone fracture. Each year, roughly 1.5 million people suffer a bone fracture related to osteoporosis (FDA Consumer magazine, January-February 2005 issue).

It has previously been shown that circulating levels of 24,25-$(OH)_2D_3$ increase during fracture repair in chicks due to an increase in renal CYP24A1 activity (7). When the effect of various vitamin D metabolites on the mechanical properties of healed bones was tested, treatment with 1,25-$(OH)_2D_3$ alone resulted in poor healing (8). However, the strength of healed bones in chickens fed 24,25-$(OH)_2D_3$ in combination with 1,25-$(OH)_2D_3$ was equivalent to that measured in a control population fed 25-hydroxyvitamin $D_3$ (8). Such results support a role of 24,25-$(OH)_2D_3$ as an essential vitamin D metabolite for fracture repair in chickens. Furthermore, in light of the signaling pathway associated with 1,25-$(OH)_2D_3$ in chickens, it was postulated that 24,25-$(OH)_2D_3$ also acts through receptor-mediated signaling, and preliminary evidence suggested the presence of a non-nuclear membrane receptor for 24,25-$(OH)_2D_3$ in the chick tibial fracture-healing callus (9,10). Prior to the instant application, studies establishing a therapeutic activity for 24,25-$(OH)_2D_3$ in mammalian fracture repair and the molecular nature of a 24-hydroxylated vitamin D compound receptor had not been reported.

At present, the only drugs approved for fracture repair/treatment are recombinant Bone Morphogenetic Proteins (BMPs). Their use is restricted to anterior lumbar interbody spine fusion, open tibial shaft fractures, and recalcitrant non-union fractures (14). These treatments are extremely costly and success rates remain below 70% (15). The pharmaceutical industry is working on smaller and cheaper molecules that could activate the BMP receptors (BMP mimetics), however there have been no published results on such studies.

Although not yet approved for human use, parathyroid hormone ("PTH") administration has been shown to improve fracture repair in rat studies (16, 17). However, the most dramatic effects come relatively late during the repair process. Furthermore, while parathyroid hormone treatment has few side effects, it is costly and requires daily injections (18). Accordingly, it is not likely to be a treatment that will be well tolerated by many patients.

Selective prostaglandin receptor agonists have also been considered for stimulation of bone repair. For example, selective agonists for receptor E2 (EP2) and receptor E4 (EP4) have been shown to stimulate fracture repair in rodents and dogs (19, 20). However, whether these agonists are being further developed for clinical use is unknown, as is the potential that significant undesired side effects may be associated with their use.

It has also recently been shown that bone mass can be regulated from the hypothalamus via the nervous system through adrenergic receptors (25). Based on that finding, it was hypothesized that bone mass may be susceptible to modulation by compounds that block such receptors ("beta-blockers"). For example, propranolol, a common beta-blocker, was shown to increase bone mass in wild-type mice and repair bone defects in rats (25, 27). Indeed, a large case-control study has suggested that beta-blockers reduce the risk of osteoporosis fractures (26). However, whether beta-blockers can be used to improve bone fracture healing without eliciting significant side effects has not been determined.

Finally, lipid-lowering drugs, known as statins, have also been shown to stimulate bone formation in vitro and in rodents (21). For example, there has been a report of enhanced fracture repair in mice following simvastatin treatment (22). However, the effectiveness of statin treatment for osteoporosis and fracture repair treatment remains controversial. The lack of association in randomized trials and the heterogeneity among observational studies do not support an effect of statins in preventing fractures (23). This could be due to the pharmacokinetic properties of statins, which are rapidly metabolized after one passage through the liver (24). Thus, it remains questionable whether statins could be used efficaciously for treatment of bone injuries.

Specifically, there is a need for a therapy that is less costly and more easily administrable than the therapies discussed above and that has an acceptable side effect profile.

The instant invention addresses the deficiencies of the compounds currently under study by providing new avenues for identifying compounds having more desirable traits. Specifically, the instant invention relates to novel 24-hydroxylated vitamin D compound receptor which can be employed in the development of such compounds. In addition, the instant application provides the first data establishing that 24-hydroxylated vitamin D compounds can function as a therapeutic in mammalian fracture repair.

SUMMARY OF THE INVENTION

In one embodiment, the present invention relates to a method of identifying a compound capable of binding to a 24-hydroxylated vitamin D compound receptor, the method comprising first contacting a 24-hydroxylated vitamin D compound receptor with a candidate compound; and subsequently determining whether the candidate compound binds to the 24-hydroxylated vitamin D compound receptor.

In another embodiment, the present invention relates to a method of identifying a compound capable of binding to a 24-hydroxylated vitamin D compound receptor, where the 24-hydroxylated vitamin D compound receptor comprises an amino acid sequence shown in SEQ ID NO: 1 or a sequence having at least 90% sequence identity thereto.

In another embodiment, the present invention relates to a method of identifying a compound capable of binding to a 24-hydroxylated vitamin D compound receptor, wherein the method involves exposing a cell expressing a 24-hydroxylated vitamin D compound receptor to the candidate compound.

In another embodiment, the present invention relates to a method of identifying a compound capable of binding to a 24-hydroxylated vitamin D compound receptor, wherein binding is detected by measuring a signal transduction output that arises downstream of the binding event.

In another embodiment, the present invention relates to methods of identifying a compound capable of binding to a 24-hydroxylated vitamin D compound receptor, wherein the binding is detected by measuring the activation of a member of the ATF family of transcription factors. In particular embodiments, the transcription factor activation that is monitored is ATF4 activation. In alternative embodiments, binding is detected by measuring activation of a protein kinase capable of directly or indirectly activating a member of the ATF family of transcription factors. In particular embodiments, the protein kinase activation that is monitored is protein kinase A (cAMP-dependent protein kinase) activation.

In another embodiment, the present invention relates to a method of identifying a compound suitable for enhancing bone fracture repair comprising, first administering a candidate compound capable of binding to a 24-hydroxylated vitamin D compound receptor to an animal; and subsequently determining whether the animal exhibits a change bone fracture repair, as compared with an animal to which the candidate compound has not been administered and thereby identifying a compound for enhancing bone fracture repair.

In another embodiment, the present invention relates to transgenic non-human mammal, such as, but not limited to, a rodent, comprising a disruption in an endogenous 24-hydroxylated vitamin D compound receptor gene. The present invention also relates to cells and/or tissues isolated from such a transgenic non-human mammal.

In another embodiment, the present invention relates to an isolated nucleic acid comprising SEQ ID NO: 2. In additional embodiments, the present invention relates to vectors, expression vectors, host cells, and transgenic animals comprising the nucleic acid of SEQ ID NO: 2.

In another embodiment, the present invention relates to isolated polypeptides comprising the sequence of SEQ ID NO:1, or fragments thereof that retain the 24-hydroxylated vitamin D compound binding activity of SEQ ID NO: 1, as well as fusion polypeptides comprising such isolated polypeptides and fragments thereof.

BRIEF DESCRIPTION OF THE DRAWINGS

FIG. 1: abnormal fracture repair in Cyp24a1$^{-/-}$ mice. Goldner-stained sections through the callus from wild-type (A) and mutant (B) mice at 14 days post-fracture. The callus is highlighted by a yellow border in wild-type animals. Note the delayed callus formation in Cyp24a1-deficient animals.

FIG. 2: rescue of impaired fracture repair in Cyp24a1-deficient mice by treatment with 24,25-(OH)$_2$D$_3$. Osteotomy was performed and animals from each genotype were treated daily with vehicle, 1,25-(OH)$_2$D$_3$ (67 ng/kg) or 24,25-(OH)$_2$D$_3$ (6.7 ug/kg). The fracture callus was harvested at 14 days post-osteotomy and bone volume (BV) and tissue volume (TV) were measured by histomorphometry using the Bio-Quant Osteo image analysis software. WT, wild-type; cyp24a1−/−, mutant mice deficient for the Cyp24a1 gene. "N.S."=not statistically significant, "*"=$p<0.05$, and "**"=$p<0.01$.

FIG. 3A-B: (3A) The amino acid sequence of FAM57B (SEQ ID NO:1). The one-letter amino acid code is recited. (3B) The nucleotide sequence of Fam57b (SEQ ID NO: 2). Sequence obtained from the listing of Fam57b in the NCBI's Entrez gene database (http://www.ncbi.nlm.nih.gov/entrez).

$(OH)_2D_3$. Bound and free ligand were separated by filtration on glass microfiber filters. Specific binding was saturable (A), and can be displaced by an excess of cold $24,25(OH)_2D_3$, but not by $1,25(OH)_2D_3$ or progesterone (B). C, D. COS7 cells stably transfected with an expression vector for the 24-hydroxylated vitamin D compound receptor were plated in a cellular dielectric spectroscopy apparatus and changes in bio-impedance (dZiec), representative of binding, were measured over a range of compound concentrations. C. Response to vitamin D compounds. D. Response to steroids. The cells showed binding activity specific for $24R,25(OH)_2D_3$, the natural epimer of $24,25(OH)_2D$.

Figure 5:
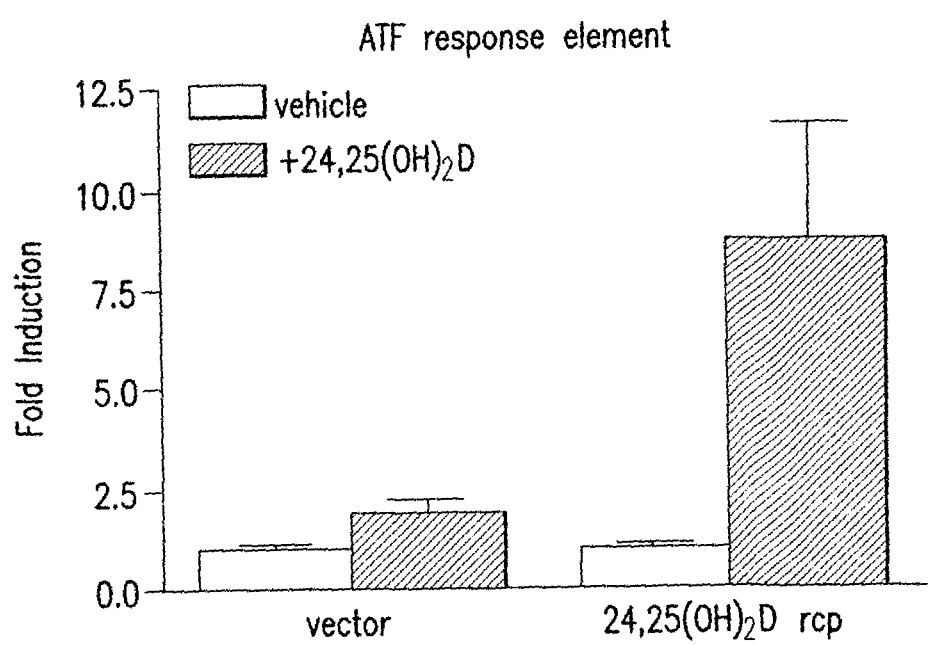

FIG. 5. Activation of the ATF response element following binding of $24,25(OH)_2D$ to the 24-hydroxylated vitamin D compound receptor. COS7 cells stably transfected with an empty expression vector (vector) or with an expression vector for the 24-hydroxyvitamin D compound receptor $(24,25(OH)_2D$ rep) were transiently transfected with a reporter construct in which the luciferase reporter is under the control of an ATF response element. Transfected cells were then treated with ethanol (vehicle) or a saturating dose of $24,25(OH)_2D$. A renilla luciferase constitutive expression vector was co-transfected to assess efficiency of transformation. Results (mean±SEM) are expressed as fold-induction over treatment with vehicle. The response of the $24,25(OH)_2D$ receptor-transfected cells is statistically significant ($p<0.05$).

SEQUENCE LISTING

The specification further incorporates by reference the Sequence Listing submitted herewith via EFS on May 30, 2013. Pursuant to 37 C.F.R. §1.52(e)(5), the Sequence Listing text file, identified as 006910_5362CSeqlis.txt, is 5,993 bytes and was created on May 30, 2013. The Sequence Listing, electronically filed herewith, does not extend beyond the scope of the specification and thus does not contain new matter.

DETAILED DESCRIPTION OF THE INVENTION

The present invention is based, in part, on the discovery that mice deficient for the 25-hydroxyvitamin D-24-hydroxylase gene, Cyp24a1, exhibit a delay in bone fracture healing. We have discovered that this delay can be corrected by exogenous administration of $24,25-(OH)_2D_3$, indicating that treatment with vitamin D metabolites hydroxylated at position 24, such as $24,25-(OH)_2D_3$, are useful in the treatment of bone fractures brought about by a trauma or metabolic bone disease such as osteoporosis. Furthermore, the inventors employed innovative techniques to identify a novel $24,25-(OH)_2D_3$ receptor that allows $24,25-(OH)_2D_3$ to act in fracture repair via receptor-mediated signaling. This $24,25-(OH)_2D_3$ receptor can be used to screen for compounds, including $24,25-(OH)_2D_3$ analogs capable of modulating activity of the receptor.

DEFINITIONS

Unless otherwise defined, all technical and scientific terms used herein have the same meanings as commonly understood by one of ordinary skill in the art to which this invention belongs. Although methods and materials similar or equivalent to those described herein can be used in the practice or testing of the present invention, suitable methods and materials are described below.

The term "24-hydroxylated vitamin D compounds", as used herein, refers to vitamin D hydroxylated at position 24 as well as metabolites and analogs thereof, including, but not limited to, $24,25-(OH)_2D_3$ and analogs thereof. Metabolites of 24-hydroxylated vitamin D compounds are those compounds produced via the endogenous metabolism of 24 hydroxylated vitamin D. Analogs of 24-hydroxylated vitamin D compounds refers to those compounds sharing structural similarity and/or functional activity with 24-hydroxylated vitamin D, which may include metabolites of 24-hydroxylated vitamin D compounds.

The term "$24,25-(OH)_2D_3$ analogs", as used herein, refers to those compounds sharing structural similarity and/or functional activity with $24,25-(OH)_2D_3$.

The term "24-hydroxylated vitamin D compound receptors", as used herein, refers to polypeptide receptors capable of binding 24-hydroxylated vitamin D compounds, and includes, but is not limited to the 24-hydroxylated vitamin D compound receptor having the sequence of SEQ ID NO: 2 or fragments thereof that retain the ability to bind 24-hydroxylated vitamin D compounds.

Use of 24-Hydroxylated Vitamin D Compounds in Mammalian Bone Fracture Repair

The present invention involves the first description of a therapeutic activity for a 24-hydroxylated vitamin D compounds in vivo in mammalian fracture repair. Fracture repair involves response to injury, intramembranous bone formation, chondrogenesis, endochondral bone formation, and bone remodelling. The immediate response to the fracture trauma results in the infiltration of inflammatory cells, macrophages, and platelets during formation of a hematoma (47). Soon after the fracture event, the bone marrow cells reorganize into regions of high and low cellular density. Within a day of the fracture event, cells in the high cellular density regions undergo differentiation along the osteoblastic lineage (47). Together with the osteoblasts that line the cortical bone, these differentiating osteoblasts lay down new bone via an intramembranous pathway to form the 'hard' callus of woven bone adjacent to the fracture site. In mice, this takes place as early as 3 days post fracture and continues until day 14 post-fracture, with proliferation peaking between days 7-10.

Mesenchymal cells proliferate for several days, and then differentiate into chondrocytes, leading to the formation of the cartilaginous, 'soft' callus that bridges the fracture site. Proliferation of these new chondrocytes continues from day 7 to day 21 post-fracture. The soft callus provides the initial stabilization at the fracture site.

The mineralization of the soft callus begins at the interface between the maturing cartilage (hypertrophic chondrocytes) and the newly formed woven bone of the hard callus. Angiogenesis occurs closely after hypertrophic chondrocyte mineralization of the matrix, mimicking endochondral bone formation at the growth plate. The hypertrophic chondrocytes undergo apoptosis, and the mineralized cartilage matrix is replaced by woven bone laid down by the osteoblasts that accompanied the infiltrating new vascular structures. The new bone repairing the fracture site will be subsequently remodelled by cooperative osteoblast/osteoclast activity, producing bone that is indistinguishable from the original intact bone (48).

Thus fracture healing involves a sequential series of cellular and biochemical events proceeding from inflammation through intramembranous bone formation, chondrogenesis, endochondral bone formation, and finally remodeling. Several studies have described a complex pattern of gene expression that occurs during the course of these events (49-52). Extracellular matrix components are differentially expressed during the different stages of fracture repair. Osteocalcin gene expression is induced and reaches a maximum around day 15 (47, 48). Collagen type II and aggrecan are expressed initially but are turned off by 9 days post fracture. This is followed by type X collagen expression when the chondrocytes become hypertrophic (53). The chondrocytes also express alkaline phosphatase, whose expression peaks around days 17-18 post fracture (54). Taken together, results from gene expression monitoring during bone repair suggest that the molecular regulation of fracture healing is complex but mimics some aspects of embryonic skeletal formation (55, 56).

As outlined in Example 1, fracture repair has been compared between cyp24a1−/− mice and wild-type controls. A delay in the mineralization of the cartilaginous matrix of the soft callus in cyp24a1−/− mutant animals has been measured, which is accompanied by reduced expression of chondrocyte marker genes. This repair delay and the aberrant pattern of gene expression is rescued by treatment with 24-hydroxylated vitamin D compound, such as $24,25(OH)_2D_3$.

The 24-hydroxylated vitamin D compounds of the invention can be formulated into compositions suitable for pharmaceutical administration. The pharmaceutical composition typically includes a 24-hydroxylated vitamin D compound, such as, but not limited to $24,25\text{-}(OH)_2D_3$, and a pharmaceutically acceptable carrier.

The 24-hydroxylated vitamin D compounds of the invention can be administered alone or linked to a carrier peptide, such as, for example, a Tat carrier peptide. Other suitable carrier peptides are known and contemplated, such as the *Drosophila* Antennapedia homeodomain, where the peptide is cross-linked via an N-terminal Cys-Cys bond to the Antennapedia carrier (97). Polyarginine is another exemplary carrier peptide (98, 99).

A pharmaceutical composition of the present disclosure can be administered via one or more routes of administration using one or more of a variety of methods known in the art. As will be appreciated by the skilled artisan, the route and/or mode of administration will vary depending upon the desired results. Routes of administration for the 24-hydroxylated vitamin D metabolites of this disclosure include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, a pharmaceutical composition comprising a 24-hydroxylated vitamin D composition of this disclosure can be administered via a non-parenteral route, such as a topical, epidermal or mucosal route of administration, for example, intranasally, orally, vaginally, rectally, sublingually or topically.

Pharmaceutical compositions can be administered with medical devices known in the art. For example, in a preferred embodiment, a therapeutic composition of this disclosure can be administered with a needleless hypodermic injection device, such as the devices disclosed in U.S. Pat. No. 5,399,163; 5,383,851; 5,312,335; 5,064,413; 4,941,880; 4,790,824; or 4,596,556. Examples of well-known implants and modules useful in the present disclosure include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions disclosed herein is contemplated.

A pharmaceutical composition of the invention is formulated to be compatible with its intended route of administration. For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. pH can be adjusted with acids or bases, such as hydrochloric acid or sodium hydroxide. Parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL. (BASF, Parsippany, N.J.), phosphate buffered saline (PBS), ethanol, polyol (for example, glycerol, propylene glycol, and liquid polyetheylene glycol, and the like), and suitable mixtures thereof. In all cases, the composition must be sterile and should be fluid to facilitate easy syringability. The proper fluidity can be maintained, for example, by the use of a coating such as lecithin, by the maintenance of the required particle size in the case of dispersion and by the use of surfactants. The composition must be stable under the conditions of manufacture and storage and must be preserved against the contaminating action of microorganisms such as bacteria and fungi. Prevention of the action of microorganisms can be achieved by various antibacterial and antifungal agents, for example, parabens, chlorobutanol, phenol, ascorbic acid, thimerosal, and the like. It may be preferable to include isotonic agents, for example, sugars, polyalcohols such as manitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound (i.e., the 24-hydroxylated vitamin D compound) in the required amount in an appropriate solvent with one or a combination of ingredients enumerated above, as required, followed by filter sterilizing the resulting solution. Generally, dispersions are prepared by incorporating the active compound into a sterile vehicle that contains a basic dispersion medium and other required ingredients from those enumerated above. In the case of sterile powders for the preparation of sterile injectable solutions, one method of preparation is vacuum drying and freeze-drying, which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of a tablet, pill, troche, or capsule. Pharmaceutically compatible binding agents, and/or adjuvant materials can be included as part of the composition. The oral compositions can contain any of the following ingredients (or ones of a similar nature): a binder such as microcrystalline cellulose; gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparing such formulations will be apparent to those skilled in the art. The polymers can also be obtained commercially from Alza Corporation and Nova Pharmaceuticals, Inc.

Liposomal suspensions can also be used as pharmaceutically acceptable carriers. These may be prepared according to methods known to those skilled in the art. For example, liposome formulations can be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of active compound is then introduced into the container. The container is then swirled by hand to free lipid material from the sides of the container and to disperse lipid aggregates, thereby forming the liposomal suspension. See, for example, U.S. Pat. No. 4,522,811.

It is especially advantageous to formulate oral or parenteral compositions in dosage unit form for ease of administration and uniformity of dosage. "Dosage unit form" as used herein refers to a physically discrete units suited for unitary dosing of the subject to be treated; each unit containing a predetermined quantity of active compound calculated to produce the desired therapeutic effect in association with the required pharmaceutical carrier. The specifications for the dosage unit forms of the invention are dictated by, and directly dependent on: (a) the unique characteristics of the active compound and the particular therapeutic effect to be achieved; and (b) the limitations inherent in the art of compounding such an active compound for the treatment of individuals. Here, the therapeutic effect and treatment relate to bone fracture and ameliorating symptoms related to bone fracture.

Actual dosage levels of the active compound in the pharmaceutical compositions of the present disclosure may be varied so as to obtain an amount of the active compound which is effective to achieve the desired therapeutic response for a particular patient, composition, and mode of administration, without being toxic to the patient. The selected dosage level will depend upon a variety of pharmacokinetic factors including the activity of the particular active compound, the route of administration, the time of administration, the rate of excretion of the active compound being employed, the duration of the treatment, other drugs, compounds and/or materials used in combination with the active compound employed, the age, sex, weight, condition, general health and prior medical history of the patient being treated, and like factors well known in the medical arts.

A "therapeutically effective dosage" of a 24-hydroxylated vitamin D compound of this disclosure preferably results in a decrease in severity of disease symptoms, an increase in frequency and duration of disease symptom-free periods, or a prevention of impairment or disability due to the disease affliction. For example, for the treatment of bone fracture, a "therapeutically effective dosage" preferably enhances bone fracture healing by at least about 5%, or more preferably by at least 10%, or more preferably by at least about 20%, more preferably by at least about 40%, even more preferably by at least about 60%, and still more preferably by at least about 80% relative to untreated subjects.

Animal models accepted in the art as models of human bone fracture repair can be used to test particular 24-hydroxylated vitamin D compounds, routes of administration etc., to determine appropriate amounts of the 24-hydroxylated vitamin D compounds of the invention.

The ability of a 24-hydroxylated vitamin D compound to enhance bone fracture repair can be evaluated in an mammalian model system predictive of efficacy in humans. Alternatively, this property of a composition can be evaluated by examining the ability of the compound to enhance bone fracture repair via in vitro assays known to the skilled practitioner and described herein. A therapeutically effective amount of a therapeutic compound can enhance bone fracture repair or otherwise ameliorate bone fracture symptoms in a subject.

The 24-Hydroxylated Vitamin D Compound Receptor

The present invention includes the first identification and characterization of a cloned polypeptide receptor for 24-hydroxylated vitamin D compounds, such as $24,25-(OH)_2D_3$. Thus, one aspect of the disclosure pertains to polypeptide receptors capable of binding 24-hydroxylated vitamin D compounds. In one embodiment, the polypeptide receptor has the amino acid sequence included in FIG. 3A as SEQ ID NO. 1.

Cyp24a1-deficient mice were used as a source of tissue to clone the 24-hydroxylated vitamin D compound receptor. Although such a receptor had previously been postulated to exist, it had not been identified despite significant efforts in the field to do so. The instant inventors undertook an innovative method to identify the 24-hydroxylated vitamin D compound receptor. Specifically, the inventors postulated that, in the absence of its specific ligand and the loss of a putative negative feedback loop, the receptor would be overexpressed in the repair callus from $Cyp24a1^{-/-}$ animals. Thus, as described in Example 2, below, gene expression profiling with cDNA microarrays was used to identify statistically significant overexpression of genes in the callus of Cyp24a1-deficient mice as compared to wild-type mice. Binding analysis of the polypeptides encoded by the overexpressed genes led to the identification of a polypeptide having the amino acid sequence of SEQ ID NO. 1 as the 24-hydroxylated vitamin D compound polypeptide receptor.

In addition to a polypeptide receptor having an amino acid sequence that is identical to SEQ ID NO. 1, the invention also encompasses polypeptide receptors that are "substantially similar" to SEQ ID NO. 1. Such polypeptides include those that retain certain structural and functional features of the polypeptide receptor of SEQ ID NO. 1, yet differ from the amino acid sequence of that polypeptide receptor at one or more amino acid position (i.e., by amino acid substitutions). For example, a polypeptide receptor that is substantially similar to SEQ ID NO. 1 is one that retains the ability to bind 24-hydroxylated vitamin D compounds. In certain embodiments, such polypeptides include, but are not limited to, polypeptides encoded by nucleic acid accession no. NM_029978.1 or NM_031478.4. In additional embodiments, such polypeptides include, but are not limited to, polypeptides having the amino acid sequence of accession no. NP_084254.1 or NP_113666.2. One example of a polypeptide that is not substantially identical to SEQ ID NO. 1 is the polypeptide defined by accession no. NM_001146347.1 (mRNA) and NP_001139819.1 (protein), which does not retain binding activity. Polypeptides that are variants of the one represented by SEQ ID NO. 1 can be prepared by substituting amino acid residues within the original SEQ ID NO. 1 polypeptide receptor and selecting polypeptides that retain 24-hydroxylated vitamin D compound binding activity. For example, amino acid residues of the polypeptide receptor can be systematically substituted with other residues and the substituted polypeptides can then be tested in standard assays for evaluating the effects of such substitutions on the ability of the polypeptide to bind 24-hydroxylated vitamin D compounds.

In some embodiments, to retain functional activity, conservative amino acid substitutions are made. As used herein, the language a "conservative amino acid substitution" is intended to include a substitution in which the amino acid residue is replaced with an amino acid residue having a similar side chain. Families of amino acid residues having similar side chains have been defined in the art, including: basic side chains (e.g., lysine, arginine, histidine); acidic side chains (e.g., aspartic acid, glutamic acid); uncharged polar side chains (e.g., glycine, asparagine, glutamine, serine, threonine, tyrosine, cysteine); nonpolar side chains (e.g., alanine, valine, leucine, isoleucine, praline, phenylalanine, methionine, tryptophan); O-branched side chains (e.g., threonine, valine, isoleucine); and aromatic side chains (e.g., tyrosine, phenylalanine, tryptophan, histidine). Other generally preferred substitutions involve replacement of an amino acid residue with another residue having a small side chain, such as alanine or glycine. Amino acid substituted peptides can be prepared by standard techniques, such as automated chemical synthesis.

The effect of the amino acid substitutions on the ability of the polypeptide to bind 24-hydroxylated vitamin D compounds can be tested in standard assays as well-known in the art and described herein (see, for example, Example 2).

In one embodiment, a polypeptide of the present invention is at least about 70%, 71%, 72%, 73%, 74%, 75%, 76%, 77%, 78%, 79%, 80%, 81%, 82%, 83%, 84%, 85%, 86%, 87%, 88%, 89% 90%, 91%, 92%, 93%, 94%, 95%, 96%, 97%, 98%, or 99% homologous to the amino acid sequence of the polypeptide receptor (SEQ ID NO:1), and is capable of binding 24-hydroxylated vitamin D compounds.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap that need to be introduced for optimal alignment of the two sequences. The comparison of sequences and determination of percent identity between two sequences can be accomplished using a mathematical algorithm, as described in the non-limiting examples described in the EXAMPLES section of this disclosure.

The percent identity between two amino acid sequences can be determined using the algorithm of E. Meyers and W. Miller (100), which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch algorithm (101), which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present disclosure can further be used as a "query sequence" to perform a search against public databases, for example, to identify related sequences. Such searches can be performed using the XBLAST program (version 2.0) of Altschul, et al. (102). BLAST protein searches can be performed with the XBLAST program, score=50, wordlength=3 to obtain homologous amino acid sequences. To obtain gapped alignments for comparison purposes, Gapped BLAST can be utilized as described in Altschul et al., (103). When utilizing BLAST and Gapped BLAST programs, the default parameters of the respective programs (e.g., XBLAST and NBLAST) are useful. See the National Center for Biotechnology Information (NCBI) website.

Polypeptide receptors of the invention can be prepared by any suitable method for polypeptide synthesis, including chemical synthesis and recombinant DNA technology. Methods for preparing peptides by recombinant expression in a host cell of DNA encoding the polypeptide are well known in the art (see e.g., Sambrook et al. (104)).

In addition to amino acid-substituted polypeptide receptors, the invention also encompasses polypeptide receptors having other modifications relative to the receptor represented by SEQ ID NO: 1. For example, the amino-terminus or carboxy-terminus of the peptide can be modified. The phrase "amino-derivative group" is intended to include amino-terminal modifications of the polypeptide receptors of the invention. Examples of such modifications include alkyl, cycloalkyl, aryl, arylalkyl, and acyl groups. A preferred N-terminal modification is acetylation. The N-terminal residue may be linked to a variety of moieties other than amino acids such as polyethylene glycols (such as tetraethylene glycol carboxylic acid monomethyl ether), pyroglutamic acid, succinoyl, methoxy succinoyl, benzoyl, phenylacetyl, 2-, 3-, or 4-pyridylalkanoyl, aroyl, alkanoyl (including acetyl and cycloalkanoyl e.g., cyclohexylpropanoyl), arylakanoyl, arylaminocarbonyl, alkylaminocarbonyl, cycloalkyl-aminocarbonyl, alkyloxycarbonyl (carbamate caps), and cycloalkoxycarbonyl, among others.

The phrase "carboxy-derivative group" is intended to include carboxy-terminal modifications of the polypeptide receptors of the invention. Examples of such modifications include modification of the carbonyl carbon of the C-terminal residue to form a carboxyterminal amide or alcohol (i.e., as reduced form). In general, the amide nitrogen, covalently bound to the carbonyl carbon on the C-terminal residue will have two substitution groups, each of which can be a hydrogen, alkyl or alkylaryl group (substituted or unsubstituted). Preferably the carboxy-derivative group is an amido group, such as —$CONH_2$, —$CONHCH_3$, —$CONHCH_2C_6H_5$ or —$CON(CH_3)_2$, but may also be 2-, 3-, or 4-pyridylmethyl, 2-, 3-, or 4-pyridylethyl, carboxylic acid, ether, carbonyl ester, alkyl, arylalkyl, aryl, cyclohexylamide, piperidineamide or other mono or disubstituted amide. Other moieties that can be linked to the C-terminal residue include piperidine-4-carboxylic acid or amide, and cis- or trans-4-amino-cyclohexanecarboxylic acid or amide.

Moreover, modification of one or more side chains of non-critical amino acid residues (e.g., "neutral" residues) may be tolerated without altering the function of the polypeptide receptors. A covalent modification of an amino acid side chain or terminal residue may be introduced into the polypeptide receptor by reacting targeted amino acid residues of the polypeptide receptor with an organic derivative agent that is capable of reacting with selected side chains or terminal residues. Examples of typical side chain modifications are described further below.

Other portions of the polypeptide can be derivatized. For example, cysteinyl residues can be reacted with α-haloacetates (and corresponding amines), such as chloroacetic acid or chloroacetamide, to produce carboxymethyl or carboxyamidomethyl derivatives. Cysteinyl residues can also be derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloro-mercuribenzoate, 2-chloromercuri-4-nitrophenol, or chloro-7-nitrobenzo-2-oxa-1,3-diazole. Cysteinyl residues can also react with nitric oxide generating three potential derivatives, sulphenic (SOH), sulphinic ($SO_2^-$) and sulphonic ($SO_3^-$), with each successive derivative possessing increasing chemical stability. Such derivatives can occur in vivo and can also be synthesized in vitro (105).

Histidyl residues can also be derivatized, e.g., by reaction with diethylpyrocarbonate at pH 5.5-7.0 because this agent is relatively specific for the histidyl side chain. Parabromophenacyl bromide is also useful; the reaction is preferably performed in 0.1 M sodium cacodylate at pH 6.0.

Lysinyl and amino terminal residues can be reacted, for example, with succinic or other carboxylic acid anhydrides. Derivatization with these agents has the effect of reversing the charge of the lysinyl residues. Other suitable reagents for derivatizing α-amino-containing residues include imodoesters such as methyl picolinimidate, pyridoxal phosphate, pyridoxal, chloroborohydride, trinitobenzenesulfonic acid, O-methylisourea, 2,4-pentanedione, and transaminase-catalyzed glyoxylate.

Arginyl residues can be modified, e.g., by reaction with one or several conventional reagents, among them phenylglyoxal, 2,3-butanedione, 1,2-cyclohexanedione, and ninhydrin. Derivatization of arginine residues requires that the reaction be performed under alkaline conditions because of the high $pK_a$ of the guanidine functional group. Furthermore, these reagents can react with lysine as well as arginine epsilon-amino groups.

Tyrosyl residues can be modified, e.g., to incorporate spectral labels via reactions with aromatic diazonium compounds or tetranitromethane. Commonly, N-acetylimidizol and tetranitromethane are used to form O-acetyl tyrosyl species and 3-nitro derivatives, respectively. The tyrosyl residues formed can be labeled with $^{125}I$ or $^{131}I$ and used in radioimmunoassays or any other suitable assay.

Carboxyl side groups (aspartyl or glutamyl) can be selectively modified, e.g., by reaction with carbodiimides (R'—N—C—N—R') such as 1-cyclohexyl-3-(2-morpholinyl-(4-ethyl) carbodiimide or 1-ethyl-3-(4-azonia-4,4-demethylpentyl) carbodiimide. Furthermore, aspartyl and glutamyl residues can be converted, for example, to asparaginyl and glutaminyl residues by reaction with ammonium ions.

Glutaminyl and asparaginyl residues can be, e.g., deamidated to form glutamyl and aspartyl residues. In certain embodiments, these residues are deamidated under mildly acidic conditions. Either form of these residues falls within the scope of this invention.

Other modifications can include hydroxylation of proline and lysine, phosphorylation of hydroxyl groups of seryl or threonyl residues, methylation of the a-amino groups of lysine, arginine, and histidine side chains (106).

Nucleic Acids Encoding 24-Hydroxylated Vitamin D Compound Receptors

Another aspect of this disclosure pertains to isolated nucleic acid molecules that encode 24-hydroxylated vitamin D compound receptors of this disclosure, portions thereof, as well as complements of these nucleic acid molecules. An exemplary 24-hydroxylated vitamin D compound receptor has the nucleotide sequence identified in FIG. 3B as SEQ ID NO. 2.

In other embodiments, the nucleic acid molecule of the invention is sufficiently complementary to a nucleotide sequence encoding a 24-hydroxylated vitamin D compound receptor of this disclosure such that it can hybridize under stringent conditions to a nucleotide sequence encoding a 24-hydroxylated vitamin D compound receptor of this disclosure, thereby forming a stable duplex.

In another embodiment, an isolated nucleic acid molecule of the present invention includes a nucleotide sequence which is at least about: 70%, 71%, 72%, 73%, 74%, 75%, 76%, 77%, 78%, 79%, 80%, 81%, 82%, 83%, 84%, 85%, 86%, 87%, 88%, 89% 90%, 91%, 92%, 93%, 94%, 95%, 96%, 97%, 98%, or 99%, or more homologous to a nucleotide sequence encoding a 24-hydroxylated vitamin D compound receptor of this disclosure, or a portion, preferably of the same length, of such nucleotide sequence.

The nucleic acids may be present in whole cells, in a cell lysate, or in substantially pure form. A nucleic acid is "isolated" or rendered "substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art (see, e.g., 107). A nucleic acid of this disclosure can be, for example, DNA or RNA and may or may not contain intronic sequences. In a preferred embodiment, the nucleic acid is a cDNA molecule.

Recombinant expression vectors which include the nucleic acids of the invention, and host cells transfected with such vectors, are also provided.

As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses. The expression vector can be a yeast expression vector, a vector for expression in insect cells, e.g., a baculovirus expression vector, or a vector suitable for expression in mammalian cells.

The recombinant expression vectors of the invention can be designed for expression of the 24-hydroxylated vitamin D compound receptors of the invention in prokaryotic or eukaryotic cells. For example, 24-hydroxylated vitamin D compound receptors of the invention can be expressed in *E. coli*, insect cells (e.g., using baculovirus expression vectors), yeast cells or mammalian cells. Suitable host cells are discussed further in Goeddel (108). Alternatively, the recombinant expression vector can be transcribed and translated in vitro, for example using T7 promoter regulatory sequences and T7 polymerase.

The term "host cell" and "recombinant host cell" are used interchangeably herein. Such terms refer not only to the particular subject cell but to the progeny or potential progeny of such a cell. Because certain modifications can occur in succeeding generations due to either mutation or environmental influences, such progeny may not, in fact, be identical to the parent cell, but are still included within the scope of the term as used herein. A host cell can be any prokaryotic or eukaryotic cell.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) a 24-hydroxylated vitamin D compound receptor of the invention. Accordingly, the invention further provides methods for producing a 24-hydroxylated vitamin D compound receptor of the invention using the host cells of the invention. In one embodiment, the method includes culturing the host cell of the invention (into which a recombinant expression vector encoding a 24-hydroxylated vitamin D compound receptor of the invention has been introduced) in a suitable medium such that a 24-hydroxylated vitamin D compound receptor of the invention is produced. In another embodiment, the method further includes isolating a 24-hydroxylated vitamin D compound receptor of the invention from the medium or the host cell.

Host cells transformed with nucleotide sequences encoding a 24-hydroxylated vitamin D compound receptor may be cultured under conditions suitable for the expression and recovery of the receptor from cell culture. The protein produced by a transformed cell may be located in the cell membrane, secreted or contained intracellularly depending on the sequence and/or the vector used. As will be understood by those of skill in the art, expression vectors containing polynucleotides that encode a 24-hydroxylated vitamin D compound receptor can be designed to contain signal sequences that direct secretion of a 24-hydroxylated vitamin D compound receptor through a prokaryotic or eukaryotic cell membrane. Other constructions may be used to join sequences encoding a 24-hydroxylated vitamin D compound receptor to nucleotide sequences encoding a polypeptide domain that will facilitate purification of soluble proteins. Such domains include, but are not limited to: metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.).

The inclusion of cleavable linker sequences, such as those specific for Factor XA or enterokinase (Invitrogen, San Diego, Calif.), between the purification domain and the 24-hydroxylated vitamin D compound receptor encoding sequence may be used to facilitate purification. One suitable construct includes a nucleic acid encoding a 24-hydroxylated vitamin D compound receptor and a nucleic acid encoding 6 histidine residues preceding a thioredoxin or an enterokinase cleavage site. The histidine residues facilitate purification on immobilized metal ion affinity chromatography (IMIAC; described in Porath, J. et al. (109)), while the enterokinase cleavage site provides a means for purifying the 24,25-$(OH)_2$ $D_3$ polypeptide receptor from the fusion protein. Although discussed above with reference to facilitating purification, the instant invention embraces alternative uses for fusion proteins comprising a 24-hydroxylated vitamin D compound receptor fused to another polypeptide sequence, such as for labeling or cellular signaling. A discussion of vectors that express fusion proteins is provided in Kroll, D. J. et al. (110).

Also within the invention are nucleic acids encoding fusion proteins in which a portion of a 24-hydroxylated vitamin D compound receptor polypeptide is fused to an heterologous polypeptide (e.g., a marker polypeptide or a fusion partner) to create a fusion protein. The invention also includes, for example, isolated polypeptides (and the nucleic acids that encode these polypeptides) that include a first portion and a second portion; the first portion includes, e.g., a 24-hydroxylated vitamin D compound receptor polypeptide, and the second portion includes an immunoglobulin constant (Fc) region or a detectable marker, wherein the detectable marker can be, but is not limited to, β-galactosidase, invertase, green fluorescent protein, luciferase, chloramphenicol, acetyltransferase, beta-glucuronidase, exo-glucanase or glucoamylase.

Transgenic Animals Relating to 24-Hydroxylated Vitamin D Compound Receptors

The present document further encompasses transgenic animals capable of expressing natural or recombinant 24-hydroxylated vitamin D compound receptors at elevated or reduced levels compared to the normal expression level. Also included are transgenic animals ("24-hydroxylated vitamin D compound receptor knockout") which do not express functional 24-hydroxylated vitamin D compound receptor as a result of one or more loss of function mutations, including a deletion, of the 24-hydroxylated vitamin D compound receptor gene. Preferably, such a transgenic animal is a non-human mammal, such as a pig, a sheep or a rodent. Most preferably the transgenic animal is a mouse or a rat. Such transgenic animals may be used in screening procedures to identify agonists and/or antagonists of 24-hydroxylated vitamin D compound receptor activity, as well as to test for their efficacy as treatments for diseases in vivo.

Detailed methods for generating non-human transgenic animals are described in further detail below and in Example 4. Transgenic gene constructs can be introduced into the germ line of an animal to make a transgenic animal. For example, one or several copies of the construct may be incorporated into the genome of a mammalian embryo by standard transgenic techniques.

In additional exemplary embodiments, transgenic non-human animals are produced by introducing transgenes encoding a 24-hydroxylated vitamin D compound receptor into the germline of the non-human animal. Embryonal target cells at various developmental stages can be used to introduce transgenes. Different methods are used depending on the stage of development of the embryonal target cell. The specific line(s) of any animal used are selected for general good health, good embryo yields, good pronuclear visibility in the embryo, and good reproductive fitness. In addition, the haplotype is a significant factor.

Introduction of the transgene into the embryo can be accomplished by any means known in the art such as, for example, microinjection, electroporation, or lipofection. For example, but not by way of limitation, a 24-hydroxylated vitamin D compound receptor transgene can be introduced into an mammal by microinjection of the construct into the pronuclei of the fertilized mammalian egg(s), causing one or more copies of the construct to be retained in the cells of the developing mammal(s). Following introduction of the transgene construct into the fertilized egg, the egg may be incubated in vitro for varying amounts of time, or reimplanted into the surrogate host, or both. In vitro incubation to maturity is included. One common method in to incubate the embryos in vitro for about 1-7 days, depending on the species, and then reimplant them into the surrogate host.

The progeny of the transgenically manipulated embryos can be tested for the presence of the construct by Southern blot analysis of the segment of tissue. If one or more copies of the exogenous cloned construct remains stably integrated into the genome of such transgenic embryos, it is possible to establish permanent transgenic animal lines, such as the mammals detailed above, carrying the transgenically added construct.

Litters of transgenically altered animals can be assayed after birth for the incorporation of the construct into the genome of the offspring. Preferably, this assay is accomplished by hybridizing a probe corresponding to the DNA sequence coding for the desired recombinant protein product or a segment thereof onto chromosomal material from the progeny. Those progeny found to contain at least one copy of the construct in their genome are grown to maturity.

For the purposes of this document a zygote is essentially the formation of a diploid cell which is capable of developing into a complete organism. Generally, the zygote will be comprised of an egg containing a nucleus formed, either naturally or artificially, by the fusion of two haploid nuclei from one or more gametes. Thus, the gamete nuclei must be ones that are naturally compatible, i.e., ones that result in a viable zygote capable of undergoing differentiation and developing into a functioning organism. Generally, a euploid zygote is preferred. If an aneuploid zygote is obtained, then the number of chromosomes should not vary by more than one with respect to the euploid number of the organism from which either gamete originated.

In addition to biological considerations, physical ones also govern the amount (e.g., volume) of exogenous genetic material that can be added to the nucleus of the zygote or to the genetic material that forms a part of the zygote nucleus. If no genetic material is removed, then the amount of exogenous genetic material that can be added is limited by the amount that will be absorbed without being physically disruptive. Generally, the volume of exogenous genetic material inserted should not exceed about 10 picoliters. The physical effects of addition must not be so great as to physically destroy the viability of the zygote. The biological limit of the number and variety of DNA sequences that can be introduced will vary depending upon the particular zygote and functions of the exogenous genetic material and will be readily apparent to one skilled in the art. This is because the genetic material, including the exogenous genetic material, of the resulting zygote must be biologically capable of initiating and maintaining the differentiation and development of the zygote into a functional organism.

The number of copies of the transgene constructs that are added to the zygote is dependent upon the total amount of exogenous genetic material added and will be the amount that enables the genetic transformation to occur. Theoretically only one copy is required; however, generally, numerous copies are utilized, for example, 1,000-20,000 copies of the transgene construct are generated to insure that one copy is functional. There will often be an advantage to having more than one functioning copy of each of the inserted exogenous DNA sequences to enhance the phenotypic expression of the exogenous DNA sequences.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and used in the art.

Reimplantation is accomplished using standard methods. Usually, the surrogate host is anesthetized, and the embryos are inserted into the oviduct. The number of embryos implanted into a particular host will vary by species, but will usually be comparable to the number of off spring the species naturally produces.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and/or expression, although any tissues or cell types may be used for this analysis.

Alternative or additional methods for evaluating the presence of the transgene include, without limitation, suitable biochemical assays such as enzymatic and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout. Where it is transgenic, it may contain the same or a different transgene, or both. Alternatively, the partner may be a parental line. When in vitro fertilization is used, the fertilized embryo may be implanted into a surrogate host or incubated in vitro, or both. Using these methods, the progeny may be evaluated for the presence of the transgene using methods described above, or other appropriate methods.

The transgenic animals produced in accordance with the present description will include exogenous genetic material. As set out above, the exogenous genetic material will, in certain embodiments, be a DNA sequence that results in the production of a 24-hydroxylated vitamin D compound receptor. Further, in such embodiments the sequence will be attached to a transcriptional control element, e.g., a promoter, which preferably allows the expression of the transgene product in a specific type of cell.

Blastocytes offer a second type of target cell for transgene introduction into a non-human animal. When a developing non-human embryo is cultured in vitro to the blastocyst stage, it can be targeted for retroviral infection (111). Efficient infection of the blastomeres is obtained by enzymatic treatment to remove the zona pellucida (Manipulating the Mouse Embryo, Hogan eds. (Cold Spring Harbor Laboratory Press, Cold Spring Harbor, 1986). The viral vector system used to introduce the transgene is typically a replication-defective retrovirus carrying the transgene (112, 113). Transfection is easily and efficiently obtained by culturing the blastomeres on a monolayer of virus-producing cells (113, 114). Alternatively, infection can be performed at a later stage. Virus or virus-producing cells can be injected into the blastocoele (115). Most of the founders will be mosaic for the transgene since incorporation occurs only in a subset of the cells that formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (115).

A third type of target cell for transgene introduction is the embryonal stem cell (ES). ES cells are obtained from pre-implantation embryos cultured in vitro and fused with embryos (116-119). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal (120).

Also provided are non-human transgenic animals, where the transgenic animal is characterized by having an altered 24-hydroxylated vitamin D compound receptor gene, preferably as described above, as models for 24-hydroxylated vitamin D compound receptor function. Alterations to the gene can include deletions or mutations that result in a loss of gene function; or the introduction of an exogenous gene, such as one having a nucleotide sequence with targeted or random mutations, or from another species; or a combination of the foregoing. The transgenic animals may be either homozygous or heterozygous for the alteration. As described in detail below, such animals and cells derived therefrom are useful for screening biologically active agents that may modulate 24-hydroxylated vitamin D compound receptor function. The screening methods are of particular use for determining the specificity and action of potential therapies for bone fracture repair.

Another aspect pertains to a transgenic nonhuman animal having a functionally disrupted endogenous 24-hydroxylated vitamin D compound receptor gene but carrying within in its genome, and expressing, a transgene encoding a heterologous 24-hydroxylated vitamin D compound receptor (e.g., a 24-hydroxylated vitamin D compound receptor from another species). Preferably, the animal is a mouse and the heterologous 24-hydroxylated vitamin D compound receptor is a human 24-hydroxylated vitamin D compound receptor. Animals, or cell lines derived from such an animal, which has been reconstituted with human 24-hydroxylated vitamin D compound receptor, can be used to identify agents that inhibit human 24-hydroxylated vitamin D compound receptor in vivo and in vitro. For example, a stimulus that induces signaling through human 24-hydroxylated vitamin D compound receptor can be administered to the animal, or cell line, in the presence and absence of an agent to be tested and the response in the animal, or cell line, can be measured. An agent that inhibits human 24-hydroxylated vitamin D compound receptor in vivo or in vitro can be identified based upon a decreased response in the presence of the agent compared to the response in the absence of the agent.

Methods of Screening Employing the
24-Hydroxylated Vitamin D Compound Receptor

The characterization of a transmembrane receptor for a 24-hydroxylated vitamin D compound provided herein identifies a novel target for pharmacological intervention in bone fracture repair. The cloned receptor can be used to screen for compounds, such as, but not limited to, vitamin D analogs having increased binding activity for the receptor.

The 24-hydroxylated vitamin D compound receptor, whether natural or recombinant, may be employed in a screening process for compounds that bind the receptor and that activate (agonists) or inhibit activation (antagonists) of the 24-hydroxylated vitamin D compound receptor. Thus, 24-hydroxylated vitamin D compound receptors may also be used to assess the binding of small molecule substrates and ligands found in, for example, cells, cell-free preparations, chemical libraries, and natural product mixtures. These substrates and ligands may be natural substrates and ligands or may be structural or functional mimetics (121). In addition, a number of vitamin D analogs have been synthesized (28). Thus an extensive libraries of compounds are readily available for screening.

Rational design of candidate compounds likely to be able to interact with a 24-hydroxylated vitamin D compound receptor may be based upon structural studies of the molecular shapes of the 24-hydroxylated vitamin D compound receptor. One means for determining which sites interact with specific other sites is a physical structure determination, e.g., X-ray crystallography or two-dimensional NMR techniques. These will provide guidance as to which amino acid residues form molecular contact regions. For a detailed description of protein structural determination, see, e.g., Blundell and Johnson (1976) (122).

An alternative to rational design uses a screening procedure that involves producing appropriate cells that express the 24-hydroxylated vitamin D compound receptor on the surface thereof. Such cells include cells from animals, yeast, *Drosophila* or *E. coli*. Cells expressing the receptor (or cell membrane containing the expressed receptor) are then contacted with a test compound to observe binding, or stimulation or inhibition of a functional response. For example, *Xenopus* oocytes may be injected with 24-hydroxylated vitamin D compound receptor mRNA or polypeptide, and currents induced by exposure to test compounds can be measured by use of voltage clamps measured.

Ligand-receptor interactions generally trigger signal transduction cascades that translate binding into an intracellular response to regulate cellular events such as proliferation, differentiation, secretion, or apoptosis. The propagation and amplification of the binding signal involve a wide array of specialized enzymes, such as protein kinases, and often culminate in the regulation of gene transcription through specific transcription factors. Thus, the identification of the cascade relevant to the 24-hydroxylated vitamin D compound receptor, as outlined in Example 3, allows for alternative screening assay, such as, but not limited to, those based on proliferation and/or differentiation. For example, microphysiometric assays may be employed to assay 24-hydroxylated vitamin D compound receptor activity. Activation of a wide variety of secondary messenger systems by ligand binding to membrane receptors results in extrusion of small amounts of acid from a cell. The acid formed is largely the result of the increased metabolic activity required to fuel the intracellular signaling process. The pH changes in the media surrounding the cell are very small but are detectable by, for example, the CYTOSENSOR microphysiometer (Molecular Devices Ltd., Menlo Park, Calif.). The CYTOSENSOR is thus capable of detecting the activation of a receptor that is coupled to an energy utilizing intracellular signaling pathway.

In certain embodiments of the present invention, cellular dielectric spectroscopy is used to ascertain binding specificity (124). The technology is based on applying electrical current to cells within a microplate format and measuring changes in impedance. For example, but not by way of limitation, the CellKey System (MDS Analytical Technologies, Concord, ON, Canada) can be used in the context of the instant invention. The CellKey System is an impedance-based, label-free technology available in 96-well format that measures changes in the impedance (dZ) of a cell layer that occur in response to receptor stimulation. In certain embodiments, COS-7 cells stably transfected with the 24-hydroxylated vitamin D compound receptor are seeded at 150,000 cells per well in 150 µl of growth medium (high-glucose DMEM with HEPES, 10% FBS, and 400 µg/ml of Geneticin). The following day, cells are washed with HBSS buffer (Hank's balanced salt solution containing 20 mM HEPES, pH 7.4, and 0.1% BSA), then equilibrated for 1 to 2 hours in 150 µl of HBSS. The plate is installed onto the system to obtain a baseline reading. Compounds (in 15 µl of HBSS) are added to all wells simultaneously and the instrument actively measures the impedance in each well. Measurements are carried for 15 minutes after compound addition to monitor cellular responses.

In certain embodiments of the present invention, the commercial Cignal Finder reporter system from SABiosciences (Frederick, Md.) is used to identify the signal transduction pathway acting downstream of the 24-hydroxylated vitamin D compound ligand-24-hydroxylated vitamin D compound receptor interaction. In particular, non-limiting, embodiments, this system consists of sets of vectors that each contain a distinct cis-acting enhancer element upstream of the luciferase reporter gene. These vectors are transiently transfected into suitable cells. A given stimulus, such as the binding of a 24-hydroxylated vitamin D compound to its receptor, initiates a signal transduction cascade that ultimately results in the binding of a specific transcription factor to its response element. This in turn leads to increased expression of the reporter gene, providing a convenient readout.

In certain embodiments of the present invention where the Cignal Finder reporter system is employed, COS-7 cells stably transfected with the 24-hydroxylated vitamin D compound receptor are seeded in 24-well tissue culture plates (Nunc, Roskilde, Denmark) at a density of 20,000 cells per well in growth medium (high-glucose DMEM with HEPES, 10% FBS, and 400 µg/ml of Geneticin). The next day the medium is changed to 0.5 ml growth medium without selection antibiotic. The cells are then transfected with the Cignal AARE Reporter vector (SABiosciences, Frederick, Md., USA): 250 ng of DNA is mixed with 50 µl of OptiMEM (Invitrogen, Grand Island, N.Y., USA) medium and 1.6 µl of Surefect transfection reagent is mixed with 50 µl of Opti-MEM. After a five minute incubation period, the DNA and transfection reagent are mixed, further incubated for twenty minutes, and the mixture is deposited on top of the cells. After 24 hours, the medium is changed to serum-free DMEM, and the cells are starved overnight (16-18 h). Then, different concentrations of 24-hydroxylated vitamin D compound are added to the cells. Following incubation, cells are washed with PBS and lysed with lysis buffer. The activity of firefly and renilla luciferases are measured sequentially on a Sirius Luminometer (Berthold Detection Systems GmbH, Pforzheim, Germany). The specific luciferase activity is expressed as the ratio of firefly/renilla luciferase activity. The specific luciferase activity of each treatment group is normalized to the specific activity of a control, vehicle-treated group. These values are shown in the graphs as relative luciferase activity.

In certain embodiments, it is useful to confirm the binding of the transcription factor to its cognate response element upon ligand-receptor interaction using a separate assay. For example, but not by way of limitation, oligonucleotides corresponding to the binding site of the transcription factor can be synthesized and tested for binding using nuclear extracts in Electrophoretic Mobility Shift Assays (EMSAs). In particular embodiments of such assays, nuclear extracts are prepared as described previously (73) using the technique of Andrews and Faller (75). Labeled probe is then added to the binding reaction mixture and the binding reactions are size-fractionated on non-denaturing 6% polyacrylamide gels. The gel is then dried and autoradiographed. Binding of the transcription factor to the probe is induced by 24-hydroxylated vitamin D compound treatment of the cells and result in a complex with reduced electrophoretic mobility (73, 75-70).

In certain embodiments of the present invention, Promega's SignaTECT protein kinase assay systems (Promega Corporation, Madison, Wis.) are used to characterize specific protein kinase pathways operating downstream of the 24-hydroxylated vitamin D compound ligand-24-hydroxylated vitamin D compound receptor interaction. Although commonly used kinase systems can also be employed in the context of the instant invention, the SignaTECT system overcomes the drawbacks of commonly used kinase assay methods that rely on the capture of phosphorylated peptide substrates on phosphocellulose (80). The SignaTECT assay is straightforward and requires phosphorylation and binding of the biotinylated substrate to a biotin capture membrane. Unincorporated [γ-32P]ATP is removed by a simple wash procedure. Washing also removes nonbiotinylated proteins that have been phosphorylated by other kinases in the sample. The bound, labeled substrate is quantitated by scintillation counting, phosphorimaging analysis or by using autoradiography. SignaTECT Protein Kinase Assay Systems are available for cAMP-Dependent protein kinase, protein kinase C, calcium/calmodulin-dependent protein kinase II (CaM KII), DNA-dependent protein kinase, tyrosine kinases, and cdc2 protein kinase.

In certain embodiments, the present invention relates to methods of identifying a compound capable of binding to a 24-hydroxylated vitamin D compound receptor, wherein the binding is detected by measuring activation of a member of the ATF family of transcription factors. In particular embodiments, the transcription factor activation that is monitored is ATF4 activation. In alternative embodiments, binding is detected by measuring activation of a protein kinase capable of directly or indirectly activating a member of the ATF family of transcription factors. In particular embodiments, the protein kinase activation that is monitored is protein kinase A (cAMP-dependent protein kinase) activation.

Still another approach is to use solubilized, unpurified or solubilized, purified polypeptide or peptides, for example extracted from transformed eukaryotic or prokaryotic host cells. This allows for a "molecular" binding assay with the advantages of increased specificity, the ability to automate, and high drug test throughput.

Ligand binding assays provide a direct method for ascertaining receptor pharmacology and are adaptable to a high throughput format. A known ligand for a receptor, when in purified form, can be radiolabeled to high specific activity (50-2000 Ci/mmol) for binding studies. A determination is then made that the process of radiolabeling does not diminish the activity of the ligand towards its receptor. Assay conditions for buffers, ions, pH and other modulators such as nucleotides are optimized to establish a workable signal to noise ratio for both membrane and whole cell receptor sources. For these assays, specific receptor binding is defined as total associated radioactivity minus the radioactivity measured in the presence of an excess of unlabeled competing ligand. Where possible, more than one competing ligand is used to define residual nonspecific binding.

The assays may simply test binding of a candidate compound wherein adherence to the cells bearing the receptor is detected by means of a label directly or indirectly associated with the candidate compound or in an assay involving competition with a labeled competitor. Further, these assays may test whether the candidate compound results in a signal generated by activation of the receptor, using detection systems appropriate to the cells bearing the receptor at their surfaces Inhibitors of activation are generally assayed in the presence of a known agonist and the effect on activation by the agonist by the presence of the candidate compound is observed.

Tissues derived from 24-hydroxylated vitamin D compound receptor knockout animals may be used in receptor binding assays to determine whether the potential drug (a candidate ligand or compound) binds to the 24-hydroxylated vitamin D compound receptor. Such assays can be conducted by obtaining a first receptor preparation from the transgenic animal engineered to be deficient in 24-hydroxylated vitamin D compound receptor production and a second receptor preparation from a source known to bind any identified 24-hydroxylated vitamin D compound receptor ligands or compounds. In general, the first and second receptor preparations will be similar in all respects except for the source from which they are obtained. For example, if brain tissue from a transgenic animal (such as described above and below) is used in an assay, comparable brain tissue from a normal (wild type) animal is used as the source of the second receptor preparation. Each of the receptor preparations is incubated with a ligand known to bind to 24-hydroxylated vitamin D compound receptors, both alone and in the presence of the candidate ligand or compound. Preferably, the candidate ligand or compound will be examined at several different concentrations.

The extent to which binding by the known ligand is displaced by the test compound is determined for both the first and second receptor preparations. Tissues derived from transgenic animals may be used in assays directly or the tissues may be processed to isolate membranes or membrane proteins which are themselves used in the assays. A preferred transgenic animal is the mouse. The ligand may be labeled using any means compatible with binding assays. This would include, without limitation, radioactive, enzymatic, fluorescent or chemiluminescent labeling.

Furthermore, antagonists of 24-hydroxylated vitamin D compound receptor activity may be identified by administering candidate compounds, etc, to wild type animals expressing functional 24-hydroxylated vitamin D compound receptor, and animals identified which exhibit any of the phenotypic characteristics associated with reduced or abolished expression of 24-hydroxylated vitamin D compound receptor function.

EXAMPLES

The present invention will be better understood by reference to the following Examples, which are provided as exemplary of the invention, and not by way of limitation.

Example 1

Role of 24-Hydroxylated Vitamin D Compounds in Mammalian Fracture Repair

A Cyp24a1-deficient mouse strain was used to determine the role of 24-hydroxylated vitamin D compounds during mammalian fracture repair. In wild-type mice, there is a significant increase in local expression of Cyp24a1 mRNA in the tibiae subjected to an osteotomy as compared to the unfractured contralateral tibiae. To identify the role of this change in gene expression on callus formation, four-month-old wild-type and Cyp24a1-deficient mice were subjected to a stabilized, transverse mid-diaphysial fracture of the tibia. Bones were collected at days 14 and 21 post-fracture and analyzed for histology and gene expression. Examination of the callus sections stained by the Goldner method showed that the homozygous mutant animals had delayed callus formation when compared to wild-type littermates (FIG. 1).

Rescue of the impaired fracture healing in Cyp24a1-deficient mice by subcutaneous injection of $24,25-(OH)_2D_3$ (6.7 µg/kg) or $1\alpha,25-(OH)_2D_3$ (67 ng/kg) was attempted. Control groups were injected with the vehicle (propylene glycol). Treatment with $1\alpha,25-(OH)_2D_3$ had no effect on fracture repair. Daily injection with $24,25-(OH)_2D_3$ normalized the histological appearance of the callus and the measured static histomorphometric index (BV/TV, FIG. 2). The treatment with $24,25-(OH)_2D_3$ also rescued and normalized type X collagen mRNA expression at all time points studied. These results indicate that 24-hydroxylated vitamin D compounds play an important role in the mechanisms leading to normal fracture healing.

Example 2

Isolation of a 24-Hydroxylated Vitamin D Compound Receptor

Cyp24a1-deficient mice were used as a source of tissue to clone a 24-hydroxylated vitamin D compound receptor. Although such a receptor had previously been postulated to exist, it had not yet been identified, despite significant efforts in the field to do so. The instant inventors undertook an innovative method to identify a 24-hydroxylated vitamin D compound receptor. Specifically, the inventors postulated that in the absence of its specific ligand and the loss of a putative negative feedback loop, the receptor would be overexpressed in the repair callus from Cyp24a1$^{-/-}$ animals. Thus gene expression profiling with cDNA microarrays was used to identify statistically significant overexpression of genes in the callus of Cyp24a1-deficient mice as compared to wild-type mice. RNA was extracted from the repair callus of three control (Cyp24a1$^{+/-}$) and three mutant (Cyp24a1$^{-/-}$) mice at 14 days post-osteotomy (a time point where significant differences in the expression of differentiation markers has been measured using RT-qPCR). This led to the identification of a restricted set of genes (Table 1). Table 1 provides a summary of gene expression monitoring by cDNA microarrays in fracture callus from wild-type or cyp24a1-deficient mice.

TABLE 1

| Gene Title | Gene ID | Function | F.C. (KO/WT) |
|---|---|---|---|
| Small proline rich protein family | Sprr2a | involved in epithelial different., increased in allergic reaction in bronchi | 5.3 |
| BC057627 | | metal binding, nucleic acid binding | 5.2 |
| Chemokine ligand 1 | Cxcl1 | Angiogenic chemokine (mouse homologue of IL-8) | 2.59 |
| 1500002O20Rik | | no described function | 2.39 |
| Tenascin N/maybe W | Tnn | W inhibits preOBs prolifer. & different. during endoch.oss., increased in fracture repair | 2.37 |
| 2310046K23Rik | | hypothetical protein of no described function | 2.35 |
| 1500016O10Rik | | no described function, Integral to membrane protein | 2.23 |
| 1110020A10Rik | | no described function | 2 |
| 5730419F03Rik | | no described function, expressed in mouse skin | 0.49 |
| Histone deacytelase 4 | HDAC4 | regulates chondrocyte hypertrophy &endoch. bone formation by inh.of RunX2 | 0.48 |
| 2310009E04Rik | | Carbohydrate kinase | 0.452 |
| 2310009E04Rik | | no described function | 0.45 |
| Mm.196290 | | Oligonucleotide/Oligosachharide-binding fold containing protein | 0.44 |
| U46068 | | no known function | 0.42 |
| Ectodysplasin A2 isoform receptor | Eda2r | involved in hair, sweat gland and teeth loss in humans and mice | 0.412 |
| SH3 domain protein D19 | SH3d19 | no described function, expressed in mouse skin | 0.38 |
| mouse ATPase p5 member | ATP13a3 | ATPase activity in all tissues | 0.38 |
| Rufy1 RUN and FYVE domain 1 | Rrad | lipid, metal, protein binding-involved in endocytosis $ protein transport & cell migration | 0.27 |
| Keratin 8 | Krt8 | Intermediate filament protein involved in epithelial cytoskeletal organization | 0.18 |
| similar to keratin, cytokeratin 8 | LOC434261 | no described function | 0.16 |
| similar to keratin, cytokeratin 8 | LOC675884 | no described function | 0.157 |
| Keratin 18 | Krt18 | Intermediate filament protein involved in epithelial cytoskeletal organization | 0.15 |
| TGF-beta 1 induced transcript 4 | TSC22 | involved in ocular, maxilla, mandible, skull, and facial gland development | 0.1 |

Statistical analysis by t test showing significant changes in expression. Gene highlighted in red were initially selected for further analysis. F.C., fold change; KO/WT, knock-out (cyp24a1-deficient) over wild-type ratio.

Genes highlighted in bold in Table 1 were further characterized since they were found to be overexpressed in Cyp24a1$^{-/-}$ callus and were of previously unknown function. Full-length cDNAs for these selected targets were subcloned into an expression vector and expressed by transient transfection into COS-7 cells. Membrane fractions were prepared by differential centrifugation and binding assays were performed using [$^3$H]-24,25-(OH)$_2$D$_3$ in the presence or absence of a 200-fold excess of nonradioactive 24,25-(OH)$_2$D$_3$. Bound and free ligand were separated by filtration on glass microfiber filters. Specific binding (total binding minus binding in the presence of excess nonradioactive ligand) measured in membrane fractions from cells transfected with a given cDNA was considered evidence that a given cDNA encodes a receptor for 24,25-(OH)$_2$D$_3$.

Clone 1500016O10Rik (also named Fam57b in the Entrez Gene database) is a 1892 bp cDNA annotated in databases as encoding a hypothetical transmembrane protein whose predicted amino acid sequence is listed in FIG. 3. The data show that FAM57B expressed in COS-7 cells binds [$^3$H]-24R,25-(OH)2D3 in a specific and saturable manner (FIG. 4). No specific binding was measured when the cells were transfected with the empty vector or with expression vectors for the other clones highlighted in Table 1. These results show that Fam57b encodes a transmembrane receptor for 24-hydroxylated vitamin D compounds.

Example 3

Characterization of a 24-Hydroxylated Vitamin D Compound Receptor

The initial step in characterizing the binding activity of a 24-hydroxylated vitamin D compound receptor involves stably transfecting 24-hydroxylated vitamin D compound receptor cDNA into COS-7 cells. Membrane fractions of transfected COS-7 cells are prepared by differential centrifugation (66): cells are homogenized in buffer A (25 mM HEPES, 10 mM NaCl, 1 mM DTT at pH 7.4) and centrifuged at 20,000 g for 10 minutes. The resulting supernatant is then re-centrifuged at 20,000 g for 2×30 minutes. The resulting pellet is resuspended in buffer B (25 mM HEPES, 50 mM NaCl, 5 mM EDTA, 1 mM DTT at pH 7.4) and is used as a membrane fraction for binding assays.

Binding assays are performed on ice for 60 min in buffer B using [$^3$H]-24R,25(OH)$_2$D$_3$ (50 Ci/mmol; Amersham) in the presence or absence of a 200-fold excess of nonradioactive 24,25(OH)$_2$D$_3$. Bound and free ligand are separated by filtration on glass microfiber filters soaked in buffer B. The filters are rinsed with 10 ml of buffer B and are counted for radioactivity using a scintillation counter (36, 37, 66). Specific binding is then calculated as total binding minus non-specific binding measured in the presence of the excess of nonradioactive ligand.

Figure 4A:
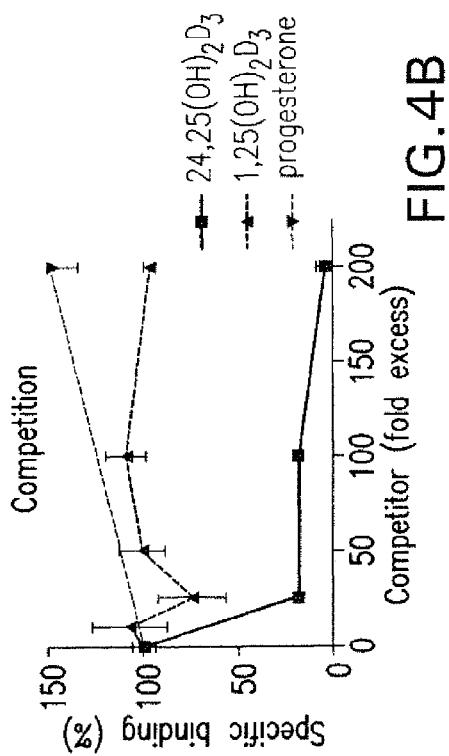
FIG. 4. Binding saturation and specificity of the 24-hydroxylated vitamin D compound receptor. A, B. The full-length 24-hydroxylated vitamin D compound receptor was subcloned into the pcDNA3.1 expression vector and expressed by stable transfection into COS7 cells. Membrane fractions were prepared by differential centrifugation and binding assays were performed using [$^3$H]-24,25(OH)$_2$D$_3$ in the presence or absence of an excess of nonradioactive 24,25
Figure 4C:
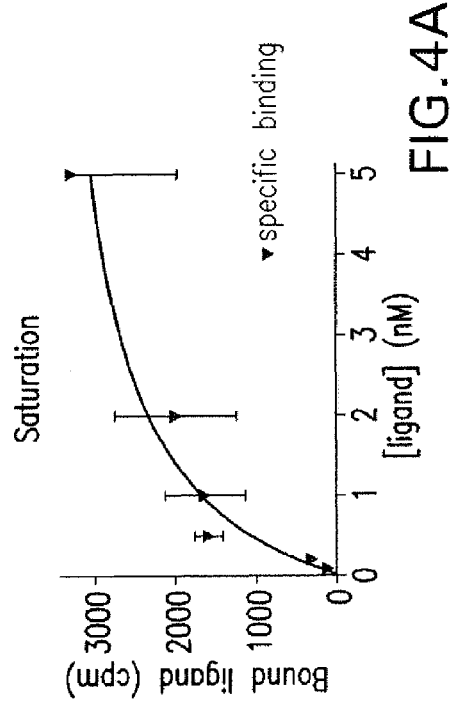

Saturation binding analysis is performed using 100 μg of membrane fraction and 0.1 to 5 nM of [$^3$H]-24R,25(OH)$_2$D$_3$ and plotting specific binding as a function of ligand concentration (FIG. 4A). Saturation binding is repeated several times to minimize intra-assay variation and calculate binding affinity with accuracy. Affinity is determined using the saturation binding algorithm of the Prism software (GraphPad Software Inc., LaJolla, Calif.).

Figure 4B:
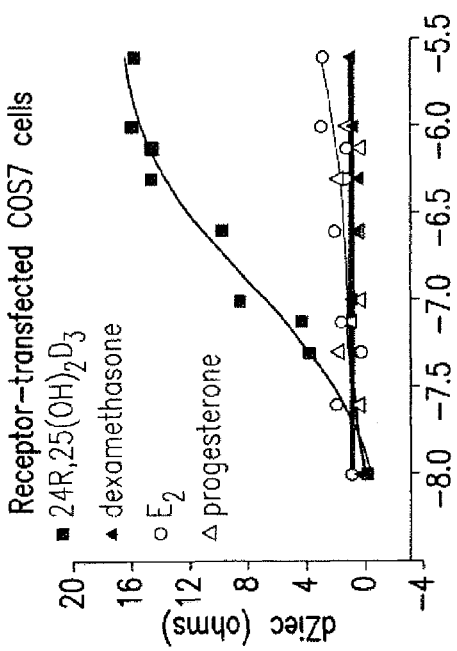
Figure 4D:
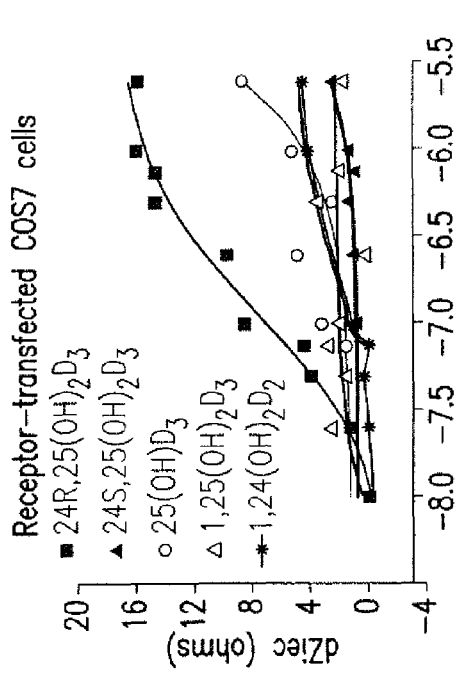

Binding specificity is further refined by performing competition binding assays on the membrane fractions with various nonradioactive vitamin D metabolites and other steroids (FIG. 4B). Binding is performed using 1 nM of [$^3$H]-24R,25 (OH)$_2$D$_3$ and 100 μg of membrane fraction. Compete binding is done using 10-200 fold excess of 24,25(OH)$_2$D$_3$ (control displacement curve). Compete binding is also done using 10-200 fold excess of 25(OH)D$_3$, 24S,25(OH)$_2$D$_3$ (the non-natural epimer of 24,25(OH)$_2$D$_3$), 1α(OH)D$_2$, 1α,24(OH)D$_2$, 1,24,25(OH)$_3$D$_3$, as well as dexamethasone, estradiol, and testosterone. These experiments are to confirm the specificity of the 24-hydroxylated vitamin D compound receptor for 24,25(OH)$_2$D$_3$ and identify vitamin D metabolites hydroxylated at position 24 that could be higher affinity ligands for the receptor.

Another method used to ascertain binding specificity is cellular dielectric spectroscopy (124). The technology is based on applying electrical current to cells within a microplate format and measuring changes in impedance. The CellKey System (MDS Analytical Technologies, Concord, ON, Canada) is an impedance-based, label-free technology available in 96-well format that measures changes in the impedance (dZ) of a cell layer that occur in response to receptor stimulation. COS-7 cells stably transfected with the 24-hydroxylated vitamin D compound receptor are seeded at 150,000 cells per well in 150 μl of growth medium (high-glucose DMEM with HEPES, 10% FBS, and 400 μg/ml of Geneticin). The following day, cells are washed with HBSS buffer (Hank's balanced salt solution containing 20 mM HEPES, pH 7.4, and 0.1% BSA), then equilibrated for 1 to 2 hours in 150 μl of HBSS. The plate is installed onto the system to obtain a baseline reading. Compounds (in 15 μl of HBSS) are added to all wells simultaneously and the instrument actively measures the impedance in each well. Measurements are carried for 15 minutes after compound addition to monitor cellular responses. Using this technology, it is seen that the recombinant receptor specifically binds 24,25(OH)$_2$D, with no cross-reactivity to the other vitamin D metabolites that we have tested (FIG. 4A) or to other steroid hormones (FIG. 4B).

A combination of Northern blot assays, TaqMan assays, in situ hybridization, and immunochemistry are used to assess the expression pattern of the 24-hydroxylated vitamin D compound receptor during development and in adult tissues. In a first experiment, a commercial Northern blot containing poly A$^+$ RNA from mouse embryos (7-day, 11-day, 15-day, and 17-day; BD Biosciences Canada, Mississauga, ON) are probed with a 24-hydroxylated vitamin D compound receptor probe to determine developmental onset of expression of the RNA.

Embryos are then collected at intervals from the time of onset of expression as determined above. The fixed embryos are embedded in paraffin and sectioned for in situ hybridization with a 24-hydroxylated vitamin D compound receptor riboprobe. Briefly, sections are dewaxed in xylene, rehydrated in serial ethanol dilutions, and re-fixed in 4% paraformaldehyde (PFA) in PBS. This is followed by proteinase K treatment, short PFA fixation, and blocking with 0.1 M triethanolamine/acetic anhydride. The treated sections are de-hydrated in serial ethanol dilutions and air-dried. Probes are labeled using the MAXIscript in vitro transcription kit (Ambion Inc., Austin, Tex.) and digoxigenin-UTP (Roche Molecular Biochemicals). Hybridization takes place overnight at 42° C. Signal detection is carried out with the DIG nucleic acid detection kit (Roche) (67). These test methods determine which tissues express a 24-hydroxylated vitamin D compound receptor during development.

RNA is also extracted from several adult tissues (brain, muscle, intestine, kidney, liver, spleen, skin, testis/ovaries, bone, etc.). The RNA is reverse-transcribed using the Applied Biosystems High Capacity cDNA Reverse Transcription Kit (Applied Biosystems, Foster City, Calif.). Relative tissue expression of the 24-hydroxylated vitamin D compound receptor is quantified using Reverse Transcription-quantitative PCR (RT-qPCR) on the reverse transcribed mRNA from different tissues with a specific TaqMan (Applied Biosystems) probe. The RT-qPCR reaction is performed on an Applied Biosystems 7500 instrument (Applied Biosystems) by the comparative $\Delta C_t$ method and normalized to Gapdh. These experiments determine the tissue distribution of the 24-hydroxylated vitamin D compound receptor mRNA expression.

The expression patterns are confirmed using immunochemistry. Since it remains challenging to purify recombinant membrane proteins, these methods instead raise anti-peptide antibodies to the 24-hydroxylated vitamin D compound receptor. Antigenic peptides are identified using the Antigen Profiler™ algorithm (www.openbiosystems.com/antibodies/custom/AntigenProfiler/). Antibodies to these antigenic peptides are used to probe 24-hydroxylated vitamin D compound receptor protein expression in tissues identified through the RT-qPCR assay, as well as in intact and fractured bones. Bones are dissected, are fixed overnight in 4% paraformaldehyde, de-mineralized in 0.5M EDTA (68), and are embedded in paraffin for immunohistochemistry on 6 μm sections with the anti-24-hydroxylated vitamin D compound receptor antibodies.

Functional immunohistochemistry protocols are developed for murine bone sections (69) using the Retrievagen A antigen retrieval system (BD BioSciences Canada). Briefly, fixed, deparaffinized, rehydrated sections are treated with Retrievagen A for 10 minutes at 94° C., are blocked with the M.O.M. blocking reagent (Vector Laboratories, Burlingame, Calif.), and are incubated with the primary antibody. Detection uses enzyme-conjugated or fluorochrome-conjugated secondary antibodies. These experiments confirm the RNA expression profiling data and identify which cell type(s) express the 24-hydroxylated vitamin D compound receptor in bone.

Example 4

Characterization of the Signal Transduction Pathway Downstream from the 24-Hydroxylated Vitamin D Compound Receptor To identify the signal transduction pathway acting downstream of the 24-hydroxylated vitamin D compound ligand-24-hydroxylated vitamin D compound receptor interaction, the commercial Cignal Finder reporter system from SABiosciences (Frederick, Md.) is used. This system consists of sets of vectors that each contain a distinct cis-acting enhancer element upstream of the luciferase reporter gene. These vectors are transiently transfected into suitable cells. A given stimulus, such as the binding of a 24-hydroxylated vitamin D compound to its receptor, initiates a signal transduction cascade that ultimately results in the binding of a specific transcription factor to its response element. This in turn leads to increased expression of the reporter gene, providing a convenient readout.

COS-7 cells stably transfected with the 24-hydroxylated vitamin D compound receptor are seeded in 24-well tissue culture plates (Nunc, Roskilde, Denmark) at a density of 20,000 cells per well in growth medium (high-glucose DMEM with HEPES, 10% FBS, and 400 µg/ml of Geneticin). The next day the medium is changed to 0.5 ml growth medium without selection antibiotic. The cells are then transfected with the Cignal AARE Reporter vector (SABiosciences, Frederick, Md., USA): 250 ng of DNA is mixed with 50 µl of OptiMEM (Invitrogen, Grand Island, N.Y., USA) medium and 1.6 µl of Surefect transfection reagent is mixed with 50 µl of OptiMEM. After a five minute incubation period, the DNA and transfection reagent are mixed, further incubated for twenty minutes, and the mixture is deposited on top of the cells. After 24 hours, the medium is changed to serum-free DMEM, and the cells are starved overnight (16-18 h). Then, different concentrations of 24-hydroxylated vitamin D compound are added to the cells. Following incubation, cells are washed with PBS and lysed with lysis buffer. The activity of firefly and renilla luciferases are measured sequentially on a Sirius Luminometer (Berthold Detection Systems GmbH, Pforzheim, Germany). The specific luciferase activity is expressed as the ratio of firefly/renilla luciferase activity. The specific luciferase activity of each treatment group is normalized to the specific activity of a control, vehicle-treated group. These values are shown in the graphs as relative luciferase activity.

The Cignal AARE reporter vector detects the pathway that responds to the ATF family of transcription factors. This pathway shows specific induction in response to 24-hydroxylated vitamin D compound treatment of cells stably transfected with an expression vector for the 24-hydroxylated vitamin D compound receptor (FIG. 5). This result is particularly significant considering the established key roles of the ATF4 transcription factor in all aspects of osteoblast biology. The identification of the transcription factor involved in mediating responses downstream from the 24-hydroxylated vitamin D compound receptor allows to screen for vitamin D compounds that have agonistic or antagonistic activity for the receptor.

As a first step to confirm the binding of the transcription factor to its cognate response element upon ligand-receptor interaction, we use Electrophoretic Mobility Shift Assays (EMSAs). Oligonucleotides corresponding to the ATF4 consensus binding site are synthesized and tested for binding using nuclear extracts in EMSAs. Nuclear extracts are prepared as described previously (73) using the technique of Andrews and Faller (75). Ten micrograms (10 µg) of nuclear proteins are incubated for 30 min at 4° C. in 20 µl of binding buffer (100 mM Tris-HCl, pH 7.5, 20 mM MgCl$_2$, 500 mM NaCl, 2% NP-40, 10 mM DTT, 10 mM EDTA, 100 ng of polydI-dC, 30% Ficoll). Labeled probe (5000 dpm) is then added to the binding reaction mixture. The binding reactions are size-fractionated on non-denaturing 6% polyacrylamide gels, then the gel is dried and autoradiographed. Binding of ATF4 to the probe is induced by 24-hydroxyvitamin D compound treatment of the cells and result in a complex with reduced electrophoretic mobility (70-75).

In parallel, the pathways operating upstream of ATF4 but downstream from the liganded 24-hydroxylated vitamin D compound receptor are characterized. These pathways involve protein kinase signaling, such as protein kinase A, the cAMP-dependent protein kinase. Promega's SignaTECT protein kinase assay systems (Promega Corporation, Madison, Wis.) are used to characterize specific protein kinase pathways operating downstream of the 24-hydroxylated vitamin D compound ligand-24-hydroxylated vitamin D compound receptor interaction. This system overcomes the drawbacks of commonly used kinase assay methods that rely on the capture of phosphorylated peptide substrates on phosphocellulose (80). The SignaTECT assay is straightforward and requires phosphorylation and binding of a biotinylated substrate to a biotin capture membrane. Unincorporated [γ-$^{32}$P] ATP is removed by a simple wash procedure. Washing also removes nonbiotinylated proteins that have been phosphorylated by other kinases in the sample. The bound, labeled substrate is quantitated by scintillation counting, phosphorimaging analysis or by using autoradiography. SignaTECT Protein Kinase Assay Systems are available for cAMP-Dependent protein kinase, protein kinase C, calcium/calmodulin-dependent protein kinase II (CaM KII), DNA-dependent protein kinase, tyrosine kinases, and cdc2 protein kinase.

These experiments identify and characterize the signaling pathways that operate to amplify the signal downstream of the interaction of the 24-hydroxylated vitamin D compound ligand with its receptor. The establishment of a cell line with an ATF4 reporter system activated upon binding of the D metabolite to its receptor is a useful tool to screen for vitamin D compounds that bind the receptor with increased affinity or specificity, or that display antagonist properties.

Example 5

Characterization of Physiological Role of the 24-Hydroxylated Vitamin D Compound Receptor in Fracture Repair Since mice deficient for Cyp24a1 cannot synthesize any 24-hydroxylated vitamin D compound ligand and exhibit a delay in callus formation during fracture healing, mice with a targeted mutation in the 24-hydroxylated vitamin D compound receptor show a similar phenotype. In the present Example, a strain of mice with a conventional knockout mutation as well as a strain allowing cell-type specific inactivation of the 24-hydroxylated vitamin D compound receptor gene are established. This section first describes the gene targeting strategies, followed by the osteotomy/fracture repair procedure, and finally assays for phenotype analysis.

Embryonic stem cells targeted at a 24-hydroxylated vitamin D compound receptor locus through gene trapping have been identified within the publicly available collection of the Texas A&M Institute for Genomic Medicine (TIGM). In this clone, the promoter-less marker/reporter gene trap is inserted into the first intron of the target 24-hydroxylated vitamin D compound receptor gene. This leads to an incorrect splicing of the target gene in which the first exon will be fused to the marker sequence to create a marker fusion transcript that can be detected by staining for β-galactosidase activity. All exons downstream of the insertion site are not expressed, leading to inactivation of the trapped gene. This targeted ES cell clone is purchased, which considerably reduces the time required to engineer a conventional knockout strain. The marker fusion transcript allows further refinement in the study of the expression pattern of the target 24-hydroxylated vitamin D compound receptor gene.

In parallel, a targeting vector based on the Cre/lox technology to achieve cell-type specific inactivation of the target 24-hydroxylated vitamin D compound receptor gene is engineered. A 129Sv bacterial artificial chromosome (BAC) clone encompassing the 24,25(OH)$_2$D receptor gene locus is commercially available. Using the technique of recombineering (recombination-mediated genetic engineering) (81-83), a targeting vector is constructed in which loxP sites are inserted within intron 1 and downstream of exon 5. Cre-mediated excision between those loxP sites delete 7140 basepairs containing exons 2-5, which essentially represents the entire coding sequence of the gene. The linearized targeting vector is electroporated into R1 ES cells (84) and double selection with the aminoglycoside antibiotic G418 and the nucleoside analog gancyclovir are applied (85). Resistant colonies are picked and expended into cell lines; these are screened for the presence of the disrupted 24-hydroxylated vitamin D compound receptor gene by Southern blot analysis after preparation of DNA by the micro-isolation technique of Laird et al (86).

ES cell clones carrying the gene-trapped allele or the floxed allele are expanded and then injected into C57BL/6 embryos at the blastocyst stage. Chimeric animals born from these injections are identified on the basis of chimeric coat color (agouti patches on a black background). Chimeric males are bred to C57BL/6 females and germ line transmission assessed by the presence of the agouti coat color in the resulting F1 progeny. Animals showing germ line transmission are genotyped by Southern blot analysis of tail DNA (86, 87) and heterozygotes for the conventional knockout or the foxed 24-hydroxylated vitamin D compound receptor allele are mated inter se to produce animals of all three possible genotypes (+/+, +/− and −/−; or +/+, +/fl, and fl/fl) (33, 67, 88, 89).

The targeted 24-hydroxylated vitamin D compound receptor foxed mice are bred to the Col1-Cre (90) or Col2-Cre (67) to achieve osteoblast- or chondrocyte-specific inactivation of the receptor gene, respectively. This is performed through the following crosses: first, the Cre transgene are bred into the floxed strain (Col1-Cre×fl/fl or Col2-Cre×fl/fl) to obtain mice carrying the Cre transgene and one foxed allele (genotype: Col1-Cre; receptor$^{+/fl}$ or Col2-Cre; receptor$^{+/fl}$). These mice are mated to homozygote foxed mice to generate mice with both alleles inactivated in osteoblasts (genotype: Col1-Cre; receptor$^{fl/fl}$) or chondrocytes (genotype: Col2-Cre; receptor$^{fl/fl}$). All mice are genotyped through a combination of PCR and Southern blot analysis of tail DNA (86, 87).

Adult wild-type and mutant mice are subjected to a stabilized, transverse mid-diaphysial fracture of the tibia or femur. A current protocol makes use of the distraction osteogenesis mouse model (91). This device is a small scale version of the Ilizarov distraction device used in orthopaedic patients (92). The custom-designed circular external fixators consist of two aluminum circular rings held concentrically by two stainless-steel threaded rods. Pins for transfixing the bone (0.25 mm) are attached to the frame with hexagonal bolts. Under sterile techniques in the procedures room, the proximal metaphysis of the tibia of anesthetized animals (knockout mutants, tissue-specific deletion mutants, and control littermates) is transfixed with pins driven percutaneously with the help of a hand-held variable-speed drill. The pins are perpendicular to the long axis of the tibia and cross at a 90 degrees intersect. Two pins are used to transfix the bone proximally and distally. The pins are secured to the rings by the hexagonal bolts with the tibias centered within the frame. A longitudinal incision followed by muscle dissection expose the tibia and a transverse osteotomy is performed between the two rings. The incision is closed with sutures that are removed on day 7 (93).

Another protocol to generate a reproducible, aligned fracture is the rodded model of immobilized fracture based on the technique described by Bonnarens and Einhorn (94). Briefly, closed, transverse, middiaphyseal fractures of the femur are generated using an upgrade of the blunt guillotine instrument originally designed for rats (94). Fracture stabilization by intramedullary fixation is carried out using the stylet of a 25 G spinal needle. The knee joint is flexed and incisions are performed at the level of the patellar ligament. The ligament is dislocated laterally to expose the femoral condyles. A 26 G needle is used to make a hole at the head of the femur through which a 25 G spinal needle is inserted. The needle is then cut and the rodded femur is fractured with the blunt guillotine. After the wounds are closed, a radiograph is taken to confirm the pin placement and the fracture. Animals are permitted full weight-bearing and unrestricted activity after awakening from anesthesia.

Adult, same gender mice of 4-5 months of age are used with a minimum of 5 animals per group. Cohorts are assigned to collect samples for histology/histomorphometry, while others are assigned to mRNA isolation for Real Time reverse-transcription PCR. A final cohort is assigned for biomechanical testing at 21 days post-osteotomy. Blood is collected from all animals at sacrifice to measure calcemia, phosphatemia, and vitamin D metabolite levels. The fractured legs are dissected at intervals following surgery (3, 7, 14, 21 days) and are fixed overnight in 4% paraformaldehyde. The bones from the day 7, 14, and 21 cohorts are first to be analyzed by micro-CT to evaluate bone formation. Then, the fixed long bones are embedded in methylmethacrylate. Sections of 6 µm are deplastified and stained by Goldner (68) for comparative histology. Quantitative histomorphometry is performed as described previously (73, 95, 96) using the BioQuant Osteo histomorphometry system.

Callus samples isolated at the same intervals (3, 7, 14, 21 days post-fracture) from control and mutant mice are also used for mRNA extraction. The mRNA is reverse-transcribed and Real Time PCR is performed using TaqMan probes for chondrocyte (Sox9, collagen type II, collagen type X, Indian Hedgehog, Hypoxia Inducible Factor-1a) or osteoblast differentiation markers (Osx, Run×2, ATF4, type I collagen, bone sialoprotein, osteocalcin). Additional markers are also tested, including (but not restricted to) VEGF, MMP-9, MMP-13, cyp24a1, cyp27b1, and VDR.

The biomechanical properties of the repaired bones are tested at 21 days post fracture and compared between genotypes. For biomechanical analysis, bones are collected in normal saline solution and mounted in a modified Instron™ three point bending test apparatus (73, 95, 96).

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. For example, but not by way of limitation, the methods described herein for identifying 24-hydroxylated vitamin D compounds beneficial for fracture healing that employ animal models are equally indicative of utility in human subjects.

Patents, patent applications, publications, procedures, and the like are cited throughout this application, the disclosures of which are incorporated herein by reference in their entireties.

REFERENCES

1. Horst R L, Reinhardt T A, Reddy G S 2005 Vitamin D metabolism. In: Feldman D, Pike J W, Glorieux F H (eds.) Vitamin D—Second Edition, vol. 1. Elsevier Academic Press, San Diego, pp 15-36.
2. Sutton A L, MacDonald P N 2003 Vitamin D: more than a "bone-a-fide" hormone. Mol Endocrinol 17(5):777-91.
3. Makin G, Lohnes D, Byford V, Ray R, Jones G 1989 Target cell metabolism of 1,25-dihydroxyvitamin D3 to calcitroic acid. Evidence for a pathway in kidney and bone involving 24-oxidation. Biochem J 262(1):173-80.
4. Reinhardt T A, Horst R L 1989 Ketoconazole inhibits self-induced metabolism of 1,25-dihydroxyvitamin D3 and amplifies 1,25-dihydroxyvitamin D3 receptor up-regulation in rat osteosarcoma cells. Arch Biochem Biophys 272(2):459-65.
5. St-Arnaud R, Arabian A, Travers R, Barletta F, Raval-Pandya M, Chapin K, Depovere J, Mathieu C, Christakos S, Demay M B, Glorieux F H 2000 Deficient mineralization of intramembranous bone in vitamin D-24-hydroxylase-ablated mice is due to elevated 1,25-dihydroxyvitamin D and not to the absence of 24,25-dihydroxyvitamin D. Endocrinology 141(7):2658-66.
6. Boyan B D, Schwartz Z 2005 Cartilage and vitamin D: genomic and nongenomic regulation by 1,25(OH)2D3 and 24,25(OH)2D3. In: Feldman D, Pike J W, Glorieux F H (eds.) Vitamin D, second edition, vol. 1. Elsevier Academic Press, San Diego, pp 575-597.
7. Seo E G, Norman A W 1997 Three-fold induction of renal 25-hydroxyvitamin D3-24-hydroxylase activity and increased serum 24,25-dihydroxyvitamin D3 levels are correlated with the healing process after chick tibial fracture. J Bone Miner Res 12(4):598-606.
8. Seo E G, Einhorn T A, Norman A W 1997 24R,25-dihydroxyvitamin D3: an essential vitamin D3 metabolite for both normal bone integrity and healing of tibial fracture in chicks. Endocrinology 138(9):3864-72.
9. Seo E G, Kato A, Norman A W 1996 Evidence for a 24R,25(OH)2-vitamin D3 receptor/binding protein in a membrane fraction isolated from a chick tibial fracture-healing callus. Biochem Biophys Res Commun 225(1): 203-8.
10. Kato A, Seo E G, Einhorn T A, Bishop J E, Norman A W 1998 Studies on 24R,25-dihydroxyvitamin D3: evidence for a normuclear membrane receptor in the chick tibial fracture-healing callus. Bone 23(2):141-6.
11. Boyan B D, Bonewald L F, Sylvia V L, Nemere I, Larsson D, Norman A W, Rosser J, Dean D D, Schwartz Z 2002 Evidence for distinct membrane receptors for 1 alpha,25-(OH)(2)D(3) and 24R,25-(OH)(2)D(3) in osteoblasts. Steroids 67(3-4):235-46.
12. Paley D 1990 Problems, obstacles, and complications of limb lengthening by the Ilizarov technique. Clin Orthop Relat Res (250):81-104.
13. Munns C F, Rauch F, Zeitlin L, Fassier F, Glorieux F H 2004 Delayed osteotomy but not fracture healing in pediatric osteogenesis imperfecta patients receiving pamidronate. J Bone Miner Res 19(11):1779-86.
14. Seeherman H, Wozney J M 2005 Delivery of bone morphogenetic proteins for orthopedic tissue regeneration. Cytokine Growth Factor Rev 16(3):329-45.
15. Govender S, Csimma C, Genant H K, Valentin-Opran A, Amit Y, Arbel R, Aro H, Atar D, Bishay M, Borner M G, Chiron P, Choong P, Cinats J, Courtenay B, Feibel R, Geulette B, Gravel C, Haas N, Raschke M, Hammacher E, van der Velde D, Hardy P, Holt M, Josten C, Ketterl R L, Lindeque B, Lob G, Mathevon H, McCoy G, Marsh D, Miller R, Munting E, Oevre S, Nordsletten L, Patel A, Pohl A, Rennie W, Reynders P, Rommens P M, Rondia J, Rossouw W C, Daneel P J, Ruff S, Ruter A, Santavirta S, Schildhauer T A, Gekle C, Schnettler R, Segal D, Seiler H, Snowdowne R B, Stapert J, Taglang G, Verdonk R, Vogels L, Weckbach A, Wentzensen A, Wisniewski T 2002 Recombinant human bone morphogenetic protein-2 for treatment of open tibial fractures: a prospective, controlled, randomized study of four hundred and fifty patients. J Bone Joint Surg Am 84-A(12):2123-34.
16. Andreassen T T, Ejersted C, Oxlund H 1999 Intermittent parathyroid hormone (1-34) treatment increases callus formation and mechanical strength of healing rat fractures. J Bone Miner Res 14(6):960-8.
17. Andreassen T T, Fledelius C, Ejersted C, Oxlund H 2001 Increases in callus formation and mechanical strength of healing fractures in old rats treated with parathyroid hormone. Acta Orthop Scand 72(3):304-7.
18. Mulder J E, Kolatkar N S, LeBoff M S 2006 Drug insight: Existing and emerging therapies for osteoporosis. Nat Clin Pract Endocrinol Metab 2(12):670-80.
19. Paralkar V M, Borovecki F, Ke H Z, Cameron K O, Lacer B, Grasser W A, Owen T A, Li M, DaSilva-Jardine P, Zhou M, Dunn R L, Dumont F, Korsmeyer R, Krasney P, Brown T A, Plowchalk D, Vukicevic S, Thompson D D 2003 An EP2 receptor-selective prostaglandin E2 agonist induces bone healing. Proc Natl Acad Sci USA 100(10:6736-40.
20. Tanaka M, Sakai A, Uchida S, Tanaka S, Nagashima M, Katayama T, Yamaguchi K, Nakamura T 2004 Prostaglandin E2 receptor (EP4) selective agonist (ONO-4819.CD) accelerates bone repair of femoral cortex after drill-hole injury associated with local upregulation of bone turnover in mature rats. Bone 34(6):940-8.
21. Mundy G, Garrett R, Harris S, Chan J, Chen D, Rossini G, Boyce B, Zhao M, Gutierrez G 1999 Stimulation of bone formation in vitro and in rodents by statins. Science 286 (5446):1946-9.
22. Skoglund B, Forslund C, Aspenberg P 2002 Simvastatin improves fracture healing in mice. J Bone Miner Res 17(10:2004-8.
23. Toh 5, Hernandez-Diaz S 2007 Statins and fracture risk. A systematic review. Pharmacoepidemiol Drug Saf 16(6): 627-40.
24. Corsini A, Bellosta S, Baetta R, Fumagalli R, Paoletti R, Bernini F 1999 New insights into the pharmacodynamic and pharmacokinetic properties of statins. Pharmacol Ther 84(3):413-28.
25. Takeda S, Elefteriou F, Levasseur R, Liu X, Zhao L, Parker K L, Armstrong D, Ducy P, Karsenty G 2002 Leptin regulates bone formation via the sympathetic nervous system. Cell 111(3):305-17.
26. Schlienger R G, Kraenzlin M E, Jick S S, Meier C R 2004 Use of beta-blockers and risk of fractures. JAMA 292(11): 1326-32.
27. Minkowitz B, Boskey A L, Lane J M, Pearlman H S, Vigorita V J 1991 Effects of propranolol on bone metabolism in the rat. J Orthop Res 9(6):869-75.
28. Bouillon R, Okamura W H, Norman A W 1995 Structure-function relationships in the vitamin D endocrine system. Endocr Rev 16(2):200-57.
29. Rucker D, Allan J A, Fick G H, Hanley D A 2002 Vitamin D insufficiency in a population of healthy western Canadians. CMAJ 166(12):1517-24.
30. Jones, G., S. A. Strugnell, and H. F. DeLuca. 1998. Current understanding of the molecular actions of vitamin D. Physiol Rev 78: 1193-1231.
31. Bouillon, R., G. Carmeliet, L. Verlinden, E. van Etten, A. Verstuyf, H. F. Luderer, L. Lieben, C. Mathieu, and M. Demay. 2008. Vitamin D and human health: lessons from vitamin D receptor null mice. Endocr Rev 29: 726-776.
32. Boyan, B. D., and Z. Schwartz. 2005. Cartilage and vitamin D: genomic and nongenomic regulation by 1,25(OH) 2D3 and 24,25(OH)2D3. In Vitamin D, second edition. D. Feldman, J. W. Pike, and F. H. Glorieux, editors. Elsevier Academic Press, San Diego. 575-597.

33. St-Arnaud, R., A. Arabian, R. Travers, F. Barletta, M. Raval-Pandya, K. Chapin, J. Depovere, C. Mathieu, S. Christakos, M. B. Demay, and F. H. Glorieux. 2000. Deficient mineralization of intramembranous bone in vitamin D-24-hydroxylase-ablated mice is due to elevated 1,25-dihydroxyvitamin D and not to the absence of 24,25-dihydroxyvitamin D. Endocrinology 141: 2658-2666.
34. Seo, E. G., and A. W. Norman. 1997. Three-fold induction of renal 25-hydroxyvitamin D3-24-hydroxylase activity and increased serum 24,25-dihydroxyvitamin D3 levels are correlated with the healing process after chick tibial fracture. J Bone Miner Res 12: 598-606.
35. Seo, E. G., T. A. Einhorn, and A. W. Norman. 1997. 24R,25-dihydroxyvitamin D3: an essential vitamin D3 metabolite for both normal bone integrity and healing of tibial fracture in chicks. Endocrinology 138: 3864-3872.
36. Seo, E. G., A. Kato, and A. W. Norman. 1996. Evidence for a 24R,25(OH)2-vitamin D3 receptor/binding protein in a membrane fraction isolated from a chick tibial fracture-healing callus. Biochem Biophys Res Commun 225: 203-208.
37. Kato, A., E. G. Seo, T. A. Einhorn, J. E. Bishop, and A. W. Norman. 1998. Studies on 24R,25-dihydroxyvitamin D3: evidence for a nonnuclear membrane receptor in the chick tibial fracture-healing callus. Bone 23: 141-146.
38. Aspenberg, P. 2005. Drugs and fracture repair. Acta Orthop 76: 741-748.
39. Mulder, J. E., N. S. Kolatkar, and M. S. LeBoff. 2006. Drug insight: Existing and emerging therapies for osteoporosis. Nat Clin Pract Endocrinol Metab 2: 670-680.
40. Paley, D. 1990. Problems, obstacles, and complications of limb lengthening by the Ilizarov technique. Clin Orthop Relat Res: 81-104.
41. Munns, C. F., F. Rauch, L. Zeitlin, F. Fassier, and F. H. Glorieux. 2004. Delayed osteotomy but not fracture healing in pediatric osteogenesis imperfecta patients receiving pamidronate. J Bone Miner Res 19: 1779-1786.
42. Horst, R. L., T. A. Reinhardt, and G. S. Reddy. 2005. Vitamin D metabolism. In Vitamin D—Second Edition. D. Feldman, J. W. Pike, and F. H. Glorieux, editors. Elsevier Academic Press, San Diego, 15-36.
43. Sutton, A. L., and P. N. MacDonald. 2003. Vitamin D: more than a "bone-a-fide" hormone. Mol Endocrinol 17: 777-791.
44. Makin, G., D. Lohnes, V. Byford, R. Ray, and G. Jones. 1989. Target cell metabolism of 1,25-dihydroxyvitamin D3 to calcitroic acid. Evidence for a pathway in kidney and bone involving 24-oxidation. Biochem J 262: 173-180.
45. Omdahl, J. L., E. A. Bobrovnikova, S. Choe, P. P. Dwivedi, and B. K. May. 2001. Overview of regulatory cytochrome P450 enzymes of the vitamin D pathway. Steroids 66: 381-389.
46. Reinhardt, T. A., and R. L. Horst. 1989. Ketoconazole inhibits self-induced metabolism of 1,25-dihydroxyvitamin D3 and amplifies 1,25-dihydroxyvitamin D3 receptor up-regulation in rat osteosarcoma cells. Arch Biochem Biophys 272: 459-465.
47. Brighton, C. T., and R. M. Hunt. 1991. Early histological and ultrastructural changes in medullary fracture callus. J Bone Joint Surg Am 73: 832-847.
48. Barnes, G. L., P. J. Kostenuik, L. C. Gerstenfeld, and T. A. Einhorn. 1999. Growth factor regulation of fracture repair. J Bone Miner Res 14: 1805-1815.
49. Hadjiargyrou, M., F. Lombardo, S. Zhao, D. W. Ahrens, J. Joo, H. Ahn, M. Jurman, D. W. White, and C. T. Rubin. 2002. Transcriptional profiling of bone regeneration. Insight into the molecular complexity of wound repair. J Biol Chem 277: 30177-30182.
50. Hatano, H., H. J. Siegel, H. Yamagiwa, J. T. Bronk, R. T. Turner, M. E. Bolander, and G. Sarkar. 2004. Identification of estrogen-regulated genes during fracture healing, using DNA microarray. J Bone Miner Metab 22: 224-235.
51. Nakazawa, T., A. Nakajima, N. Seki, A. Okawa, M. Kato, H. Moriya, N. Amizuka, T. A. Einhorn, and M. Yamazaki. 2004. Gene expression of periostin in the early stage of fracture healing detected by cDNA microarray analysis. J Orthop Res 22: 520-525.
52. Rundle, C. H., H. Wang, H. Yu, R. B. Chadwick, E. I. Davis, J. E. Wergedal, K. H. Lau, S. Mohan, J. T. Ryaby, and D. J. Baylink. 2006. Microarray analysis of gene expression during the inflammation and endochondral bone formation stages of rat femur fracture repair. Bone 38: 521-529.
53. Sandberg, M., H. Aro, P. Multimaki, H. Aho, and E. Vuorio. 1989. In situ localization of collagen production by chondrocytes and osteoblasts in fracture callus. J Bone Joint Surg Am 71: 69-77.
54. Nakagawa, Y., K. Shimizu, T. Hamamoto, K. Suzuki, M. Ueda, and T. Yamamuro. 1994. Calcium-dependent neutral proteinase (calpain) in fracture healing in rats. J Orthop Res 12: 58-69.
55. Colnot, C., Z. Thompson, T. Miclau, Z. Werb, and J. A. Helms. 2003. Altered fracture repair in the absence of MMP9. Development 130: 4123-4133.
56. Ferguson, C., E. Alpern, T. Miclau, and J. A. Helms. 1999. Does adult fracture repair recapitulate embryonic skeletal formation? Mech Dev 87: 57-66.
57. Naik, A. A., C. Xie, M. J. Zuscik, P. Kingsley, E. M. Schwarz, H. Awad, R. Guldberg, H. Drissi, J. E. Puzas, B. D. Boyan, X. Zhang, and J. O'Keefe R. 2009. Reduced COX-2 expression in aged mice is associated with impaired fracture healing. J Bone Miner Res 24: 251-264.
58. Simon, A. M., M. B. Manigrasso, and J. P. O'Connor. 2002. Cyclo-oxygenase 2 function is essential for bone fracture healing. J Bone Miner Res 17: 963-976.
59. Zhang, X., E. M. Schwarz, D. A. Young, J. E. Puzas, R. N. Rosier, and R. J. O'Keefe. 2002. Cyclooxygenase-2 regulates mesenchymal cell differentiation into the osteoblast lineage and is critically involved in bone repair. J Clin Invest 109: 1405-1415.
60. Li, M., H. Z. Ke, H. Qi, D. R. Healy, Y. Li, D. T. Crawford, V. M. Paralkar, T. A. Owen, K. O. Cameron, B. A. Lefker, T. A. Brown, and D. D. Thompson. 2003. A novel, non-prostanoid EP2 receptor-selective prostaglandin E2 agonist stimulates local bone formation and enhances fracture healing. J Bone Miner Res 18: 2033-2042.
61. Paralkar, V. M., F. Borovecki, H. Z. Ke, K. O. Cameron, B. Lefker, W. A. Grasser, T. A. Owen, M. Li, P. DaSilva-Jardine, M. Zhou, R. L. Dunn, F. Dumont, R. Korsmeyer, P. Krasney, T. A. Brown, D. Plowchalk, S. Vukicevic, and D. D. Thompson. 2003. An EP2 receptor-selective prostaglandin E2 agonist induces bone healing. Proc Natl Acad Sci USA 100: 6736-6740.
62. Tanaka, M., A. Sakai, S. Uchida, S. Tanaka, M. Nagashima, T. Katayama, K. Yamaguchi, and T. Nakamura. 2004. Prostaglandin E2 receptor (EP4) selective agonist (ONO-4819.CD) accelerates bone repair of femoral cortex after drill-hole injury associated with local upregulation of bone turnover in mature rats. Bone 34: 940-948.
63. Holick, M. F., E. S. Siris, N. Binkley, M. K. Beard, A. Khan, J. T. Katzer, R. A. Petruschke, E. Chen, and A. E. de Papp. 2005. Prevalence of Vitamin D inadequacy among 63. postmenopausal North American women receiving osteoporosis therapy. J Clin Endocrinol Metab 90: 3215-3224.
64. Rucker, D., J. A. Allan, G. H. Fick, and D. A. Hanley. 2002. Vitamin D insufficiency in a population of healthy western Canadians. CMAJ 166: 1517-1524.
65. Thomas, M. K., D. M. Lloyd-Jones, R. I. Thadhani, A. C. Shaw, D. J. Deraska, B. T. Kitch, E. C. Vamvakas, I. M. Dick, R. L. Prince, and J. S. Finkelstein. 1998. Hypovitaminosis D in medical inpatients. N Engl J Med 338: 777-783.
66. Patino, R., and P. Thomas. 1990. Characterization of membrane receptor activity for 17 alpha, 20 beta, 21-trihydroxy-4-pregnen-3-one in ovaries of spotted seatrout (Cynoscion nebulosus). Gen Comp Endocrinol 78: 204-217.
67. Terpstra, L., J. Prud'homme, A. Arabian, S. Takeda, G. Karsenty, S. Dedhar, and R. St-Arnaud. 2003. Reduced chondrocyte proliferation and chondrodysplasia in mice lacking the integrin-linked kinase in chondrocytes. J Cell Biol 162: 139-148.
68. Dickson, G. R. 1984. Methods of calcified tissue preparation Elsevier, New York, N.Y.
69. Terpstra, L., J. Prud'homme, A. Arabian, S. Takeda, G. Karsenty, S. Dedhar, and R. St-Arnaud. 2003. Reduced chondrocyte proliferation and chondrodysplasia in mice lacking the Integrin-Linked Kinase (ILK) in chondrocytes. J Cell Biol 162: 139-148.
70. Holick, S. A., M. F. Holick, and J. A. MacLaughlin. 1980. Chemical synthesis of [1 beta-3H] 1 alpha, 25-dihydroxyvitamin D3 and [1 alpha-3H] 1 beta, 25-dihydroxyvitamin D2: biological activity of 1 beta, 25-dihydroxyvitamin D3. Biochem Biophys Res Commun 97: 1031-1037.
71. Masuda, S., V. Byford, A. Arabian, Y. Sakai, M. B. Demay, R. St-Arnaud, and G. Jones. 2005. Altered pharmacokinetics of 1alpha,25-dihydroxyvitamin D3 and 25-hydroxyvitamin D3 in the blood and tissues of the 25-hydroxyvitamin D-24-hydroxylase (Cyp24a1) null mouse. Endocrinology 146: 825-834.
72. Courey, A. J., and R. Tjian. 1988. Analysis of Sp1 in vivo reveals multiple transcriptional domains, including a novel glutamine-rich activation motif. Cell 55: 887-898.
73. Yu, V. W., G. Ambartsoumian, L. Verlinden, J. M. Moir, J. Prud'homme, C. Gauthier, P. J. Roughley, and R. St-Arnaud. 2005. FIAT represses ATF4-mediated transcription to regulate bone mass in transgenic mice. J Cell Biol 169: 591-601.
74. Andrews, N. C., and D. V. Faller. 1991. A rapid micropreparation technique for extraction of DNA-binding proteins from limiting numbers of mammalian cells. Nucleic Acids Res 19: 2499.
75. Akhouayri, O., I. Quelo, and R. St-Arnaud. 2005. Sequence-Specific DNA Binding by the {alpha}NAC Coactivator Is Required for Potentiation of c-Jun-Dependent Transcription of the Osteocalcin Gene. Mol Cell Biol 25: 3452-3460.
76. Akhouayri, O., and R. St-Arnaud. 2007. Differential mechanisms of transcriptional regulation of the mouse osteocalcin gene by jun family members. Calcif Tissue Int 80: 123-131.
77. Candeliere, G. A., P. W. Jurutka, M. R. Haussler, and R. St-Arnaud. 1996. A composite element binding the vitamin D receptor, retinoid X receptor alpha, and a member of the CTF/NF-1 family of transcription factors mediates the vitamin D responsiveness of the c-fos promoter. Mol Cell Biol 16: 584-592.
78. Moreau, A., W. V. Yotov, F. H. Glorieux, and R. St-Arnaud. 1998. Bone-specific expression of the alpha chain of the nascent polypeptide-associated complex, a coactivator potentiating c-Jun-mediated transcription. Mol Cell Biol 18: 1312-1321.
79. St-Arnaud, R., and J. M. Moir. 1993. Wnt-1-inducing factor-1: a novel G/C box-binding transcription factor regulating the expression of Wnt-1 during neuroectodermal differentiation. Mol Cell Biol 13: 1590-1598.
80. Toomik, R., P. Ekman, and L. Engstrom. 1992. A potential pitfall in protein kinase assay: phosphocellulose paper as an unreliable adsorbent of produced phosphopeptides. Anal Biochem 204: 311-314.
81. Copeland, N. G., N. A. Jenkins, and D. L. Court. 2001. Recombineering: a powerful new tool for mouse functional genomics. Nat Rev Genet. 2: 769-779.
82. Court, D. L., J. A. Sawitzke, and L. C. Thomason. 2002. Genetic engineering using homologous recombination. Annu Rev Genet. 36: 361-388.
83. Warming, S., N. Costantino, D. L. Court, N. A. Jenkins, and N. G. Copeland. 2005. Simple and highly efficient BAC recombineering using galK selection. Nucleic Acids Res 33: e36.
84. Nagy, A., J. Rossant, R. Nagy, W. Abramow-Newerly, and J. C. Roder. 1993. Derivation of completely cell culture-derived mice from early-passage embryonic stem cells. Proc Natl Acad Sci USA 90: 8424-8428.
85. Mansour, S. L., K. R. Thomas, and M. R. Capecchi. 1988. Disruption of the proto-oncogene int-2 in mouse embryo-derived stem cells: a general strategy for targeting mutations to non-selectable genes. Nature 336: 348-352.
86. Laird, P. W., A. Zijderveld, K. Linders, M. A. Rudnicki, R. Jaenisch, and A. Berns. 1991. Simplified mammalian DNA isolation procedure. Nucleic Acids Res 19: 4293.
87. Southern, E. M. 1975. Detection of specific sequences among DNA fragments separated by gel electrophoresis. J. Mol. Biol. 98: 503-517.
88. Dardenne, O., J. Prud'homme, A. Arabian, F. H. Glorieux, and R. St-Arnaud. 2001. Targeted inactivation of the 25-hydroxyvitamin D(3)-1(alpha)-hydroxylase gene (CYP27B1) creates an animal model of pseudovitamin D-deficiency rickets. Endocrinology 142: 3135-3141.
89. Rauch, F., J. Prud'homme, A. Arabian, S. Dedhar, and R. St-Arnaud. 2000. Heart, brain and body wall defects in mice lacking calreticulin. Exp Cell Res 256: 105-111.
90. Dacquin, R., M. Starbuck, T. Schinke, and G. Karsenty. 2002. Mouse alpha1(I)-collagen promoter is the best known promoter to drive efficient Cre recombinase expression in osteoblast. Dev Dyn 224: 245-251.
91. Tay, B. K., A. X. Le, S. E. Gould, and J. A. Helms. 1998. Histochemical and molecular analyses of distraction osteogenesis in a mouse model. J Orthop Res 16: 636-642.
92. Aronson, J. 1994. Experimental and clinical experience with distraction osteogenesis. Cleft Palate Craniofac J 31: 473-481; discussion 481-472.
93. Haque, T., F. Hamade, N. Alam, M. Kotsiopriftis, D. Lauzier, R. St-Arnaud, and R. C. Hamdy. 2008. Characterizing the BMP pathway in a wild type mouse model of distraction osteogenesis. Bone 42: 1144-1153.
94. Bonnarens, F., and T. A. Einhorn. 1984. Production of a standard closed fracture in laboratory animal bone. J Orthop Res 2: 97-101.
95. Dardenne, 0., J. Prudhomme, S. A. Hacking, F. H. Glorieux, and R. St-Arnaud. 2003. Rescue of the pseudovitamin D deficiency rickets phenotype of CYP27B1-deficient mice by treatment with 1,25-dihydroxyvitamin D3:

biochemical, histomorphometric, and biomechanical analyses. J Bone Miner Res 18: 637-643.
96. Dardenne, O., J. Prud'homme, S. A. Hacking, F. H. Glorieux, and R. St-Arnaud. 2003. Correction of the abnormal mineral ion homeostasis with a high-calcium, high-phosphorus, high-lactose diet rescues the PDDR phenotype of mice deficient for the 25-hydroxyvitamin D-1alpha-hydroxylase (CYP27B1). Bone 32: 332-340.
97. Theodore, L., et al. *J. Neurosci.* 15:7158 (1995); Johnson, J. A., et al., *Circ. Res.* 79:1086 (1996b).
98. Mitchell et al., J. Peptide Res., 56:318-325 (2000).
99. Rothbard et al., *Nature Med.,* 6:1253-1257 (2000).
100. E. Myers and W. Miller, *Comput. Appl. Biosci.,* 4:11-17 (1988).
101. Needleman and Wunsch, *J. Mol. Biol.* 48:444-453 (1970).
102. Altschul, et al. (1990) *J. Mol. Biol.* 215:403-10.
103. Altschul et al., (1997) *Nucleic Acids Res.* 25(17):3389-3402.
104. Sambrook et al. (1989) Molecular Cloning: A Laboratory Manual, 2nd Edition, Cold Spring Harbor Laboratory Press.
105. Hess D. T, et al, Protein_S-nitrosylation: Purview and parameters, *Nat Rev Mol Cell Biol.* 2005; 6:150-66.
106. T. E. Creighton (1983) Proteins: Structure and Molecular Properties, W. H. Freeman & Co., San Francisco, pp. 79-86).
107. F. Ausubel, et al., ed. (1987) Current Protocols in Molecular Biology, Greene Publishing and Wiley Interscience, New York.
108. Goeddel, (1990) Gene Expression Technology: Methods in Enzymology 185, Academic Press, San Diego, Calif.
109. Porath, J. et al. (1992) Prot. Exp. Purif. 3: 263-281.
110, Kroll, D. J. et al. (1993) DNA Cell Biol. 12:441-453.
111. Jaenich, R. (1976) PNAS 73:1260-1264.
112. Jahner et al. (1985) PNAS 82:6927-6931.
113. Van der Putten et al. (1985) PNAS 82:6148-6152.
114. Stewart et al. (1987) EMBO J. 6:383-388.
115. Jahner et al. (1982) Nature 298:623-628.
116. Evans et al. (1981) Nature 292:154-156.
117. Bradley et al. (1984) Nature 309:255-258.
118. Gossler et al. (1986) PNAS 83: 9065-9069.
119. Robertson et al. (1986) Nature 322:445-448.
120. Jaenisch, R. (1988) Science 240:1468-1474.
121. Coligan et al., Current Protocols in Immunology 1(2): Chapter 5 (1991).
122. Blundell and Johnson (1976) Protein Crystallography, Academic Press, New York.
123. DeLuca H F 2004 Overview of general physiologic features and functions of vitamin D. Am J Clin Nutr 80:1689S-1696.
124. Ciambrone et al. 2004. J Biomol Screen 9: 467-480

---

What is claimed is:

1. A method of identifying a compound capable of binding to a 24-hydroxylated vitamin D compound receptor, the method comprising:
   (a) contacting a 24-hydroxylated vitamin D compound receptor with a candidate compound wherein said 24-hydroxylated vitamin D compound receptor comprises either the amino acid sequence of SEQ ID NO: 1, or said sequence comprising conservative amino acid substitutions thereof; and
   (b) determining whether the candidate compound binds to the 24-hydroxylated vitamin D compound receptor, wherein binding is detected by an assay selected from the group consisting of: i) a receptor competition assay, wherein said receptor is contacted with said candidate compound, wherein said candidate compound is labeled in the presence of an excess of unlabeled $24,25(OH)_2$-vitamin $D_3$, and binding of said labeled candidate compound in the presence of excess unlabeled $24,25(OH)_2$-vitamin $D_3$ indicates said compound is capable of binding to said receptor, ii) an assay that measures changes in the impedance of a cell layer that occur in response to said receptor binding to said candidate compound; iii) an assay that measures the activation of a member of the ATF family of transcription factors; and iv) an assay that measures the activation of protein kinase A.

2. The method of claim 1, wherein binding is detected by an assay that measures activation of a member of the ATF family of transcription factors.

3. The method of claim 2, wherein said member of the ATF family of transcription factors is ATF4.

4. The method of claim 1, wherein binding is detected by an assay that measures activation of protein kinase A.

5. The method of claim 1, wherein binding is detected by a receptor competition assay, wherein said receptor is contacted with said candidate compound, wherein said candidate compound is labeled in the presence of an excess of unlabeled $24,25(OH)_2$-vitamin $D_3$, and binding of said labeled candidate compound in the presence of excess unlabeled $24,25(OH)_2$-vitamin $D_3$ indicates said compound is capable of binding to said receptor.

6. The method of claim 1, wherein binding is detected by an assay that measures changes in the impedance of a cell layer that occur in response to said receptor binding to said candidate compound.

* * * * *